(12) United States Patent
Johnson et al.

(10) Patent No.: US 8,560,055 B2
(45) Date of Patent: Oct. 15, 2013

(54) SYSTEM AND METHODS FOR THE SELECTIVE UPDATING OF HEART SIGNAL PARAMETER TIME SERIES

(75) Inventors: Steven R. Johnson, Fair Haven, NJ (US); Bruce Hopenfeld, Salt Lake City, UT (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 920 days.

(21) Appl. No.: 12/702,777

(22) Filed: Feb. 9, 2010

(65) Prior Publication Data

US 2010/0241017 A1 Sep. 23, 2010

Related U.S. Application Data

(60) Provisional application No. 61/152,367, filed on Feb. 13, 2009.

(51) Int. Cl.
*A61B 5/0456* (2006.01)
*A61B 5/0468* (2006.01)
(52) U.S. Cl.
CPC ............ *A61B 5/0468* (2013.01); *A61B 5/0456* (2013.01)
USPC ......................................... 600/509; 600/521

(58) Field of Classification Search
USPC .......................... 600/508–510, 515–519, 521
See application file for complete search history.

(56) References Cited

U.S. PATENT DOCUMENTS

| 4,316,249 | A  | * | 2/1982 | Gallant et al. ................. 600/515 |
| 7,558,623 | B2 |   | 7/2009 | Fischell et al. |
| 2009/0076403 | A1 |   | 3/2009 | Hopenfeld |
| 2009/0082682 | A1 |   | 3/2009 | Fischell et al. |

\* cited by examiner

*Primary Examiner* — Carl H Layno
*Assistant Examiner* — Jessica Sarcione
(74) *Attorney, Agent, or Firm* — Rosenberg, Klein & Lee

(57) ABSTRACT

A heart rate monitor generates an ST deviation time series by employing a recursive filter that is preferably an exponential average filter whose output is a weighted sum of the then existing ST time series value and current ST deviation values of analyzable beats. Beats are detected in segments of data. ST deviation is measured for analyzable beats. The ST deviation time series is updated only if certain criteria are met. A first criterion for updating the time series is that at least half of the beats within a segment must be normal sinus rhythm beats. A second criterion for updating the time series is that (i) the average RR interval of the segment is between ¾ and 1.5 times the average RR interval of the previous segment; or (ii) both (a) the number of abnormal beats in the current segment is less than 2, and (b) the number of premature ventricular contractions within the current segment is less than 2.

11 Claims, 22 Drawing Sheets

| | ST change | Absolute ST Level | QT | downsloping ST | QRS Interval |
|---|---|---|---|---|---|
| Positive STshift | Isctr or DST > TH1 | STL(end) − STAV(bin) > maxd(bin) + 0.1 | | | |
| Positive STshift | | STL(end) − STAV(bin) > maxd(bin) + 0.2 | | | |
| Negative STshift | Isctr or DST < TH1 | STL(end) − STAV(bin) < mind(bin) − 0.1 | | | |
| Negative STshift | | STL(end) − STAV(bin) < maxd(bin) − 0.2 | | | |
| Positive STshift | Isctr or DST > TH1 | | QT(RR) < nor. min. QT(RR) − 15ms | | |
| Negative STshift | Isctr or DST < TH1 | | QT(RR) < nor. min. QT(RR) − 15ms | | |
| Negative STshift | Isctr or DST < TH1 | | | Yes | |
| Positive or Negative STshift | | | | | Increases by > 15ms (and has been smoothly changing) |

FIG. 10a

| STL(end) > maxd(bin) + 0.1 within the last 3 minutes | Irregular rhythm detected |
|---|---|
| STL(end) < mind(bin) − 0.1 within the last 3 minutes | Irregular rhythm detected |

FIG.10b

| | sinus ST ch. | Absolute ST Level – sinus | paced ST ch. | Absolute ST Level – paced |
|---|---|---|---|---|
| Positive STshift | Isctr or DST > TH1 | | | |
| Positive STshift | | STL(end) – STAV(bin) > maxd(bin) + 0.2 | | |
| Positive STshift | | | Isctr or DST > TH2 | |
| Positive STshift | | | | STL(end) – STAV(bin) > maxd(bin) + 0.2 |
| Negative STshift | Isctr or DST < TH1 | | | |
| Negative STshift | | STL(end) – STAV(bin) < maxd(bin) – 0.2 | | |
| Negative STshift | | | Isctr or DST < TH2 | |
| Negative STshift | | | | STL(end) – STAV(bin) < maxd(bin) – 0.2 |
| Positive STshift | Isctr or DST > TH3 | | | |
| Negative STshift | Isctr or DST < TH3 | | | |
| Positive STshift | | | Isctr or DST > TH3 | |
| Negative STshift | | | Isctr or DST < TH3 | |

FIG. 11

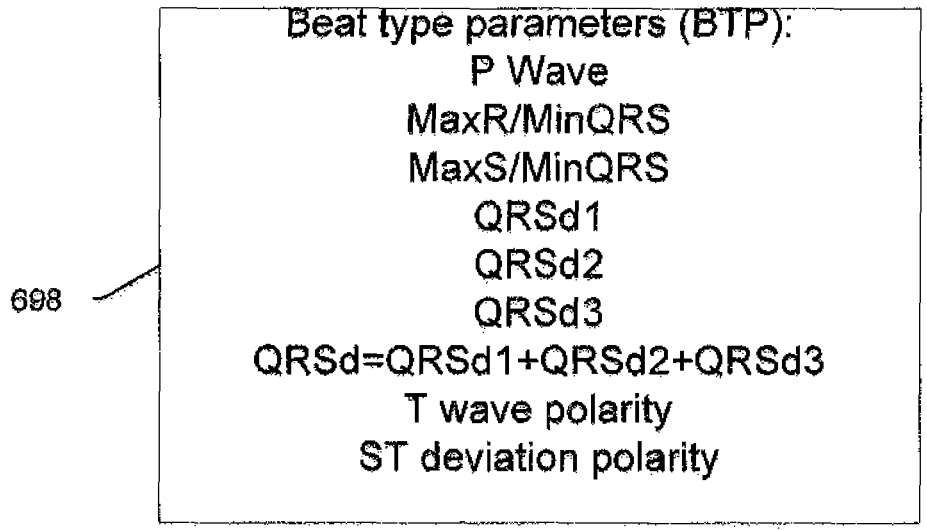
FIG. 12
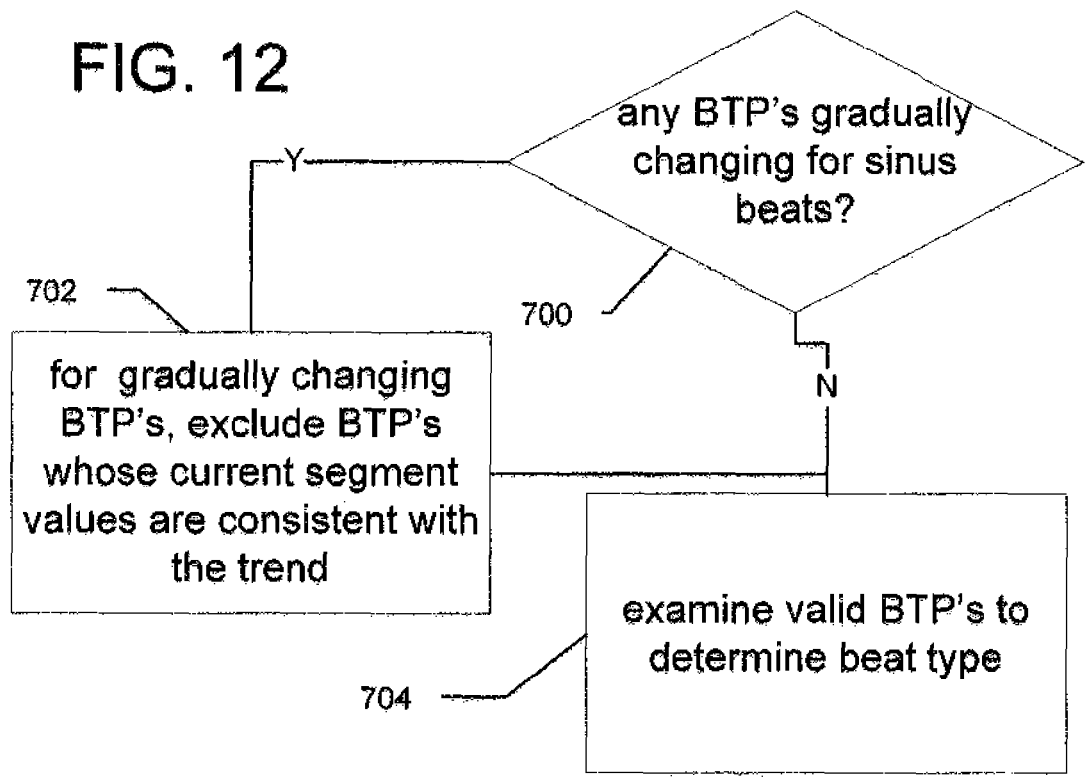

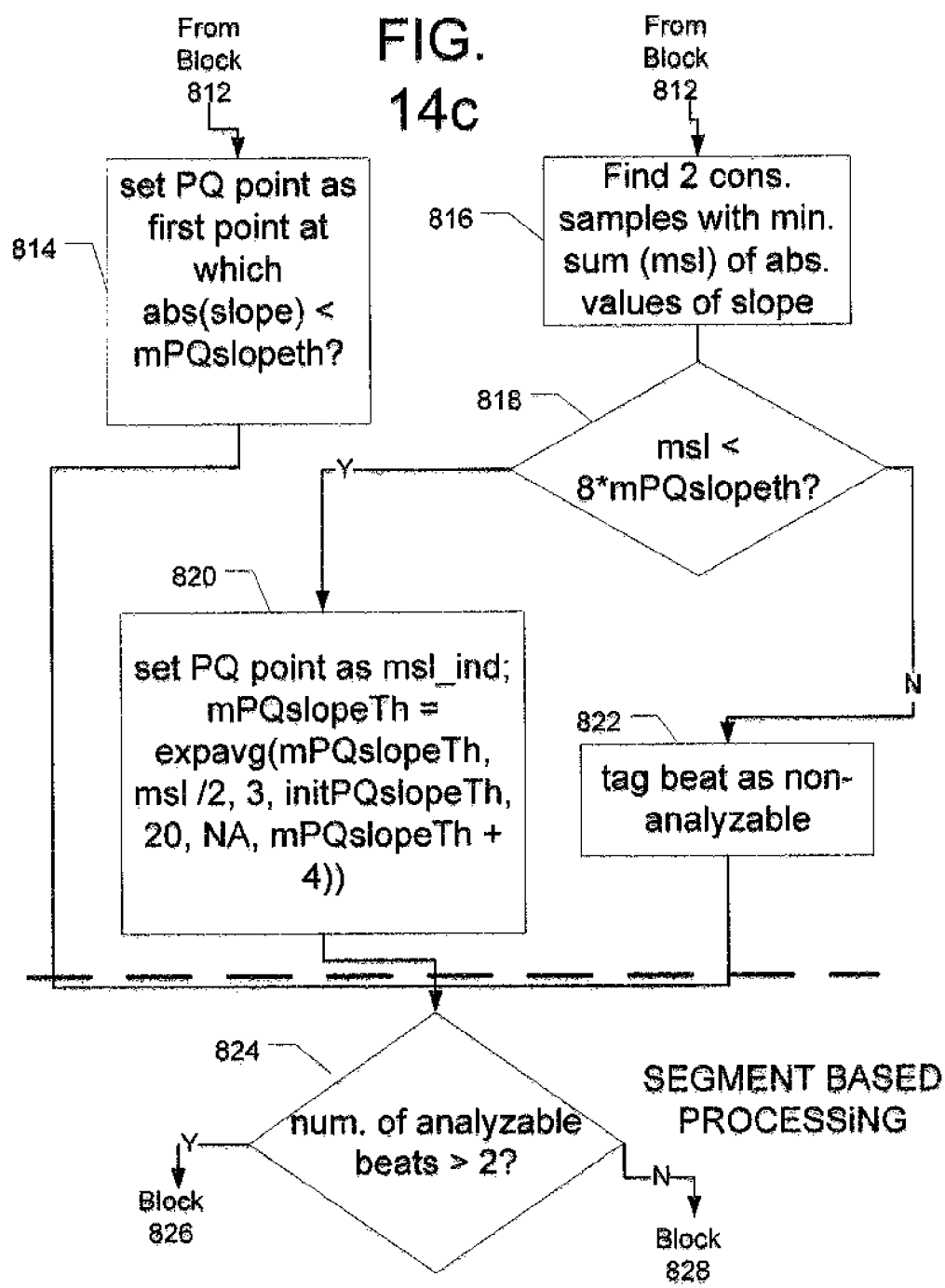

SEGMENT BASED PROCESSING

SYSTEM AND METHODS FOR THE SELECTIVE UPDATING OF HEART SIGNAL PARAMETER TIME SERIES

CROSS REFERENCE TO RELATED APPLICATIONS

This is the utility patent application based upon the provisional patent application Ser. No. 61/152,367, entitled "Time Series Tracking System and Methods for the Detection of Cardiac Events" filed provisionally on Feb. 13, 2009.

FIELD OF USE

This invention is in the field of medical device systems that monitor a patient's cardiovascular condition.

BACKGROUND OF THE INVENTION

Heart disease is the leading cause of death in the United States. A heart attack, also known as an acute myocardial infarction (AMI), typically results from a blood clot or "thrombus" that obstructs blood flow in one or more coronary arteries. AMI is a common and life-threatening complication of coronary artery disease. Coronary ischemia is caused by an insufficiency of oxygen to the heart muscle. Ischemia is typically provoked by physical activity or other causes of increased heart rate when one or more of the coronary arteries is narrowed by atherosclerosis. AMI, which is typically the result of a completely blocked coronary artery, is the most extreme form of ischemia. Patients will often (but not always) become aware of chest discomfort, known as "angina", when the heart muscle is experiencing ischemia. Those with coronary atherosclerosis are at higher risk for AMI if the plaque becomes further obstructed by thrombus.

There are a number of portable monitors that attempt to detect AMI. Monitors that include wearable sensors (e.g. a medical-vest with electrodes) may be somewhat inconvenient for patients. Chronically implanted sensors provide the possibility for continuous monitoring without many of the inconveniences associated with wearable monitors. One type of implantable monitor known as the Guardian (Angel Medical Systems, the assignee of the present invention), which is currently undergoing clinical trials in the United States, includes an electrode chronically implanted within the heart. An intracardiac electrode may provide a strong signal at the cost of requiring intracardiac implantation. Another type of implantable monitor can rely upon subcutaneous electrodes, which are less invasive, but receive smaller amplitude signals compared to intracardiac electrodes.

Detection of AMI often involves analyzing changes in a person's ST segment voltage. A common scheme for computing changes in the ST segment involves determining a quantity known as ST deviation for each beat. However, noise can confound the interpretation of ST measurements. Conventional ST segment based heart monitors include beat morphology discrimination that rejects bad beats from the determination of ST segment deviation.

Despite all of the foregoing work that has been done, there is still a need for an effective system for detecting QRS onset and offset points.

SUMMARY OF THE INVENTION

An embodiment of the present invention comprises a heart monitor that may be chronically implanted or external. The device, which includes an analog to digital convertor and a processor that performs beat detection, monitors the time course of a heart signal parameter, namely ST segment deviation, computed from an electrocardiogram. An ST deviation time series is generated by a recursive filter that is preferably an exponential average fitter whose output is a weighted sum of the then existing ST time series value and current ST deviation values of analyzable beats.

The device acquire periodically acquires waveform data in fixed duration segments. Each segment is separately processed.

After each segment is processed, the ST deviation time series is updated only if certain criteria are met. A first criterion for updating the time series is at least half of the beats (within the segment) must be analyzable. An analyzable beat is a sinus rhythm beat that meets various morphology criteria. One of the morphology criteria is the difference between the then current time series value and the ST deviation of the beat. If this difference is too large, the beat is not considered analyzable.

A second criterion for updating the time series is that (i) the average RR interval of the segment is between ¾ and 1.5 times the average RR interval of the previous segment; or (ii) both (a) the number of abnormal beats in the current segment is less than 2, and (b) the number of premature ventricular contractions within the current segment is less than 2.

BRIEF DESCRIPTION OF THE DRAWINGS

FIGS. 10a, 10b and 11 are tables that show various combinations of cardiac parameter values that will trigger detection of a cardiac event.

FIG. 12 is a flow chart of a routine that determines whether a particular beat is classified as a particular beat type.

FIGS. 14a-14d are collectively a flow chart of a routine that processes electrocardiogram/electrogram segments to perform morphology checking on QRS complexes and to determine the location of PQ points for analyzable QRS complexes.

DETAILED DESCRIPTION OF THE INVENTION

As used in the specification and claims, "relative frequency" of an event means a measure of the number of occurrences of that event relative to either time or other events. The measure of the number of occurrences need not be an exact count of the number of occurrences. For example, if there are actually 2 good beats (event) and 8 bad beats (another event), the relative frequency may be 0, which indicates that there are more other types of events (8) than the event in question (2). Continuing with this example, if there are actually 8 good beats and 2 bad beats, the relative frequency may be 1, which indicates that there are more instances of the the event in question.

Architecture

Figure 1:
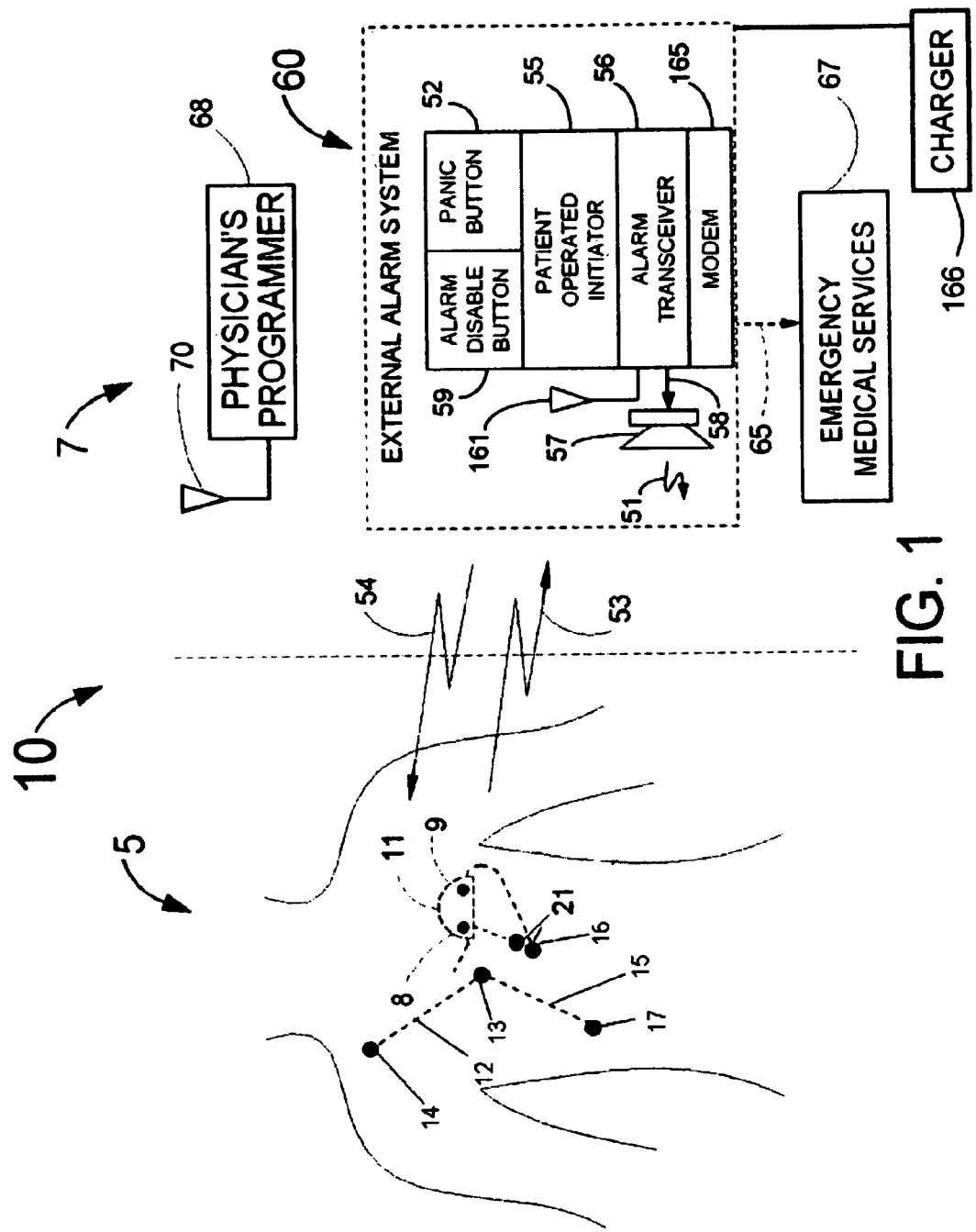
FIG. 1 illustrates a system for the detection of a cardiac event and for warning the patient that a medically relevant cardiac event is occurring.

FIG. 1 illustrates one embodiment of a system 10 comprising an implanted cardiac event detection device 5 and external equipment 7. The battery powered cardiac diagnostic device 5 contains electronic circuitry that can detect a cardiac event such as an acute myocardial infarction or arrhythmia and warn the patient when the event, or a clinically relevant precursor, occurs. The cardiac diagnostic device 5 can store the patient's electrogram for later readout and can send wireless signals 53 to and receive wireless signals 54 from the external equipment 7. The functioning of the cardiac diagnostic device 5 will be explained in greater detail with the assistance of FIG. 2.

The cardiac diagnostic device 5 receives electrical signals from intracardiac, subcutaneous or body surface leads 12 and 15, which in the embodiment illustrated here will be a clavicle and right side lead, respectively. Clavicle lead 12 comprises electrodes 13 and 14 with polarity hereafter defined as the difference potential measured between electrode 13 and electrode 14. Right side lead 15 comprises electrodes 13 and 17 with polarity hereafter defined as the potential at electrode 13 minus the potential at electrode 17. The electrode 13 is preferably disposed as close as possible to the sternum, in the fourth intercostal space on the right side of the body. The electrode 17 may be positioned to reduce ST deviation changes associated with heart rate changes by aligning the lead parallel to ST segment deviation contours, (See Hopenfeld B., "ST segment depression: the possible role of global repolarization dynamics", Biomed Eng Online. 2007 Feb. 9; 6:6.). The electrode position may be selected by, for example, performing a stress test with electrodes in a few different positions inferior and to the right of electrode 13 (while maintaining a minimum distance from electrode 13.).

The clavicle lead 12 measures the electrical signal between the upper right clavicle and a medial region over the area of the sternum and is therefore generally less than 15 cm long; the clavicle lead 12 is approximately aligned with the long axis of the heart. The right side lead 15 measures the electrical signal between the right precordial chest region and an inferior right lateral or posterior torso position. The cardiac diagnostic device 5 is housed in a metal case 11 that can serve as another electrode. The cardiac device 5 is shown in the left upper pectoral region but may be implanted in any convenient location such as the upper right pectoral region.

Many other embodiments of the present invention are possible. In one alternative embodiment, a lead is implanted within the heart, and the detection method of the present invention may be applied to signals received through that lead.

Also, as will be described more fully below, the present invention may be used in conjunction with an implantable cardioverter/defibrillator, a pacemaker or biventricular pacemakers (cardiac resynchronization therapy devices), or different types of implantable monitors (such as an implantable ventricular chamber pressure sensor or temperature sensor). In this case, an intracardiac lead 21, for example in the RV apex with the housing 11 serving as a reference potential, may provide electrical signals for analysis. Extracardiac leads could also be employed.

If the portable detection device described herein is used in conjunction with any of the above mentioned therapeutic devices, according to one embodiment of the present invention, alarm data (associated with the present invention's detection scheme) is sent from the device through a service such as St. Jude Merlin.net or Medtronic Carelink. The service, in turn, notifies the patient that he/she needs to seek treatment. According to a possible implementation of this embodiment, the portable detection device does not require an internal alarm, thereby decreasing the size of the portable device.

FIG. 1 also shows the external equipment 7 that consists of a physician's programmer 68 having an antenna 70, an external alarm system 60 including a charger 166. The external equipment 7 provides means to interact with the cardiac diagnostic device 5. These interactions include programming the cardiac diagnostic device 5, retrieving data collected by the cardiac diagnostic device 5 and handling alarms generated by the cardiac diagnostic device 5. The operation of these components is further described in U.S. patent application publication number 2004/0215092.

Figure 2:
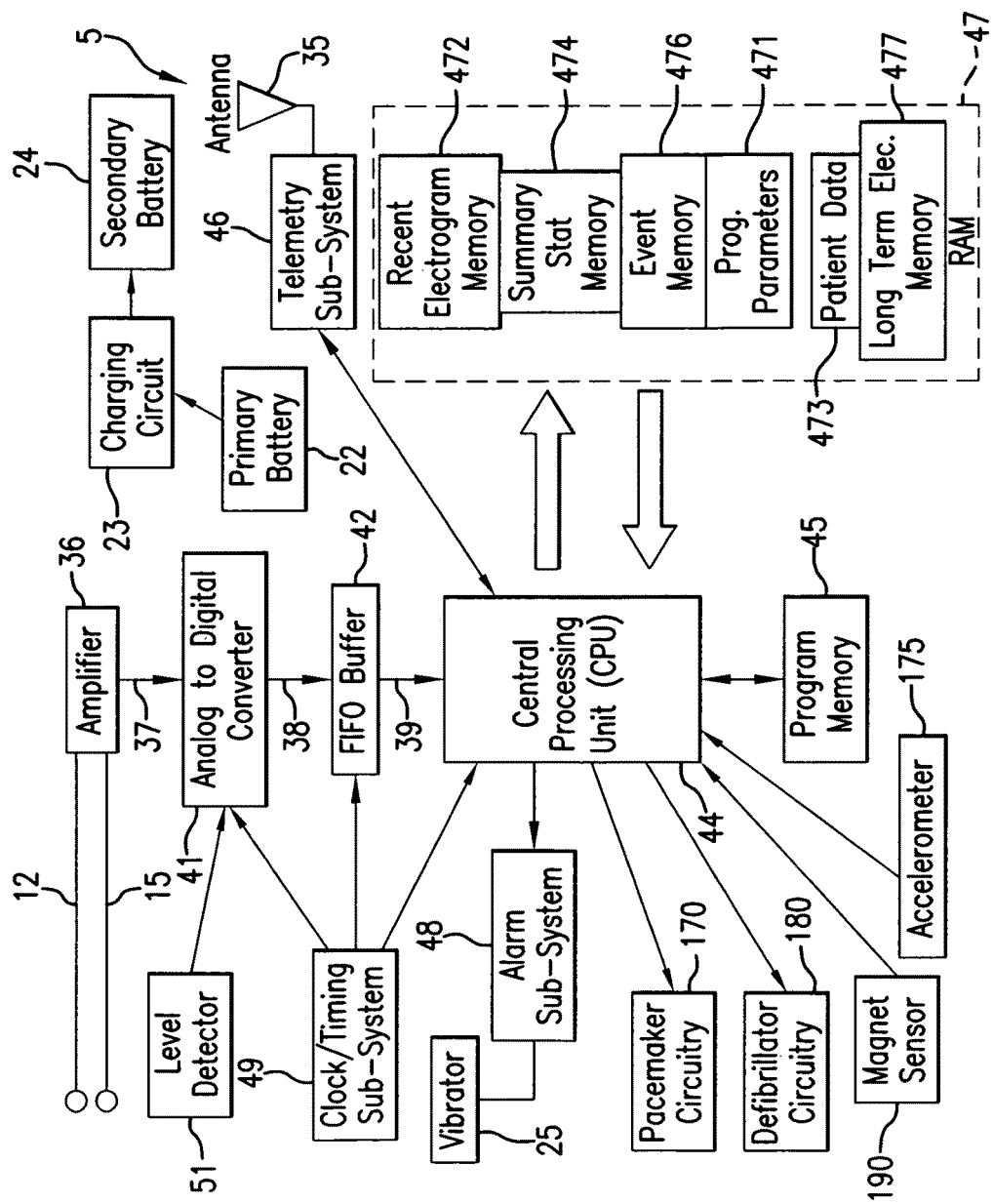
FIG. 2 is a block diagram of an implanted cardiac diagnostic system according to the present invention.

FIG. 2 is a block diagram of the cardiac diagnostic device 5 with primary battery 22 and a secondary battery 24. The secondary battery 24 is typically a rechargeable battery of smaller capacity but higher current or voltage output than the primary battery 22 and is used for short term high output components of the cardiac diagnostic device 5 like the RF chipset in the telemetry sub-system 46 or the vibrator 25 attached to the alarm sub-system 48. According to a dual battery configuration, the primary battery 22 will charge the secondary battery 24 through the charging circuit 23. The primary battery 22 is typically a larger capacity battery than the secondary battery 24. The primary battery also typically has a lower self discharge rate as a percentage of its capacity than the secondary battery 24. It is also envisioned that the secondary battery could be charged from an external induction coil by the patient or by the doctor during a periodic check-up.

The pairs of wires corresponding to leads 12 and 15 respectively connect to the amplifier 36, which is a multi-channel or differential amplifier. The amplified electrogram signals 37 from the amplifier 36 are then converted to digital signals 38 by the analog-to-digital converter 41, which preferably samples at a rate of at least 200 Hz. The temporal resolution of the sampling is relevant with regard to the sampling of the high frequency components of a heartbeat's activation (QRS) complex. The digital electrogram signals 38 are buffered in the First-In-First-Out (FIFO) memory 42. Processor means shown in FIG. 2 as the central processing unit (CPU) 44 coupled to memory means shown in FIG. 2 as the Random Access Memory (RAM) 47 can process the digital electrogram data 38 stored the FIFO 42 according to the programming instructions stored in the program memory 45. This programming (i.e. software) enables the cardiac diagnostic device 5 to detect the occurrence of a cardiac event such as an acute myocardial infarction.

A level detector 51 is coupled to the analog to digital converter 41. The level detector 51 detects whether a patient's torso is upright or supine and also, if the torso is supine, the extent of its rotation with respect to the earth (e.g. patient is lying flat on his/her back, lying on his/her right side or left side.) Many MEMS based level detects which can also operationally serve as inclinometers, accelerometers, and general detectors for motion/force exist.

Additional sensors may communicate with the device 5 wirelessly through the telemetry sub-system. The data from these leads may correspond to digitized electrogram signals (that have been processed by a remote subcutaneous device).

The operation of most of the components in FIG. 2 is further described in U.S. patent application publication number 2004/0215092.

In a preferred embodiment of the present invention the RAM 47 includes specific memory locations for 4 sets of electrogram segment storage. These memory locations are the recent electrogram storage 472 that would store the last 2 to 10 minutes of recently recorded electrogram segments so that the electrogram data occurring just before the onset of a cardiac event can be reviewed at a later time by the patient's physician using the physician's programmer 68 of FIG. 1. For example, the recent electrogram storage 472 might contain eight 10-second long electrogram segments that were captured every 30 seconds over the last 4 minutes.

A summary statistics memory 474 would provide storage for summary information, such as running averages, of various cardiac waveform feature values. A long term electrogram memory 477 would provide storage for electrograms collected over a relatively long period of time. In the preferred embodiment, every ninth electrogram segment that is acquired is stored in a circular buffer, so that the oldest electrogram segments are overwritten by the newest one.

The telemetry sub-system 46 with antenna 35 provides the cardiac diagnostic device 5 the means for two-way wireless communication to and from the external equipment 7 of FIG. 1. Existing radiofrequency transceiver chip sets such as the Ash transceiver hybrids produced by RF Microdevices, Inc. can readily provide such two-way wireless communication over a range of up to 10 meters from the patient. It is also envisioned that short range telemetry such as that typically used in pacemakers and defibrillators could also be applied to the cardiac diagnostic device 5. It is also envisioned that standard wireless protocols such as Bluetooth and 802.11a or 802.11b might be used to allow communication with a wider group of peripheral devices.

Flowcharts

Figure 3:
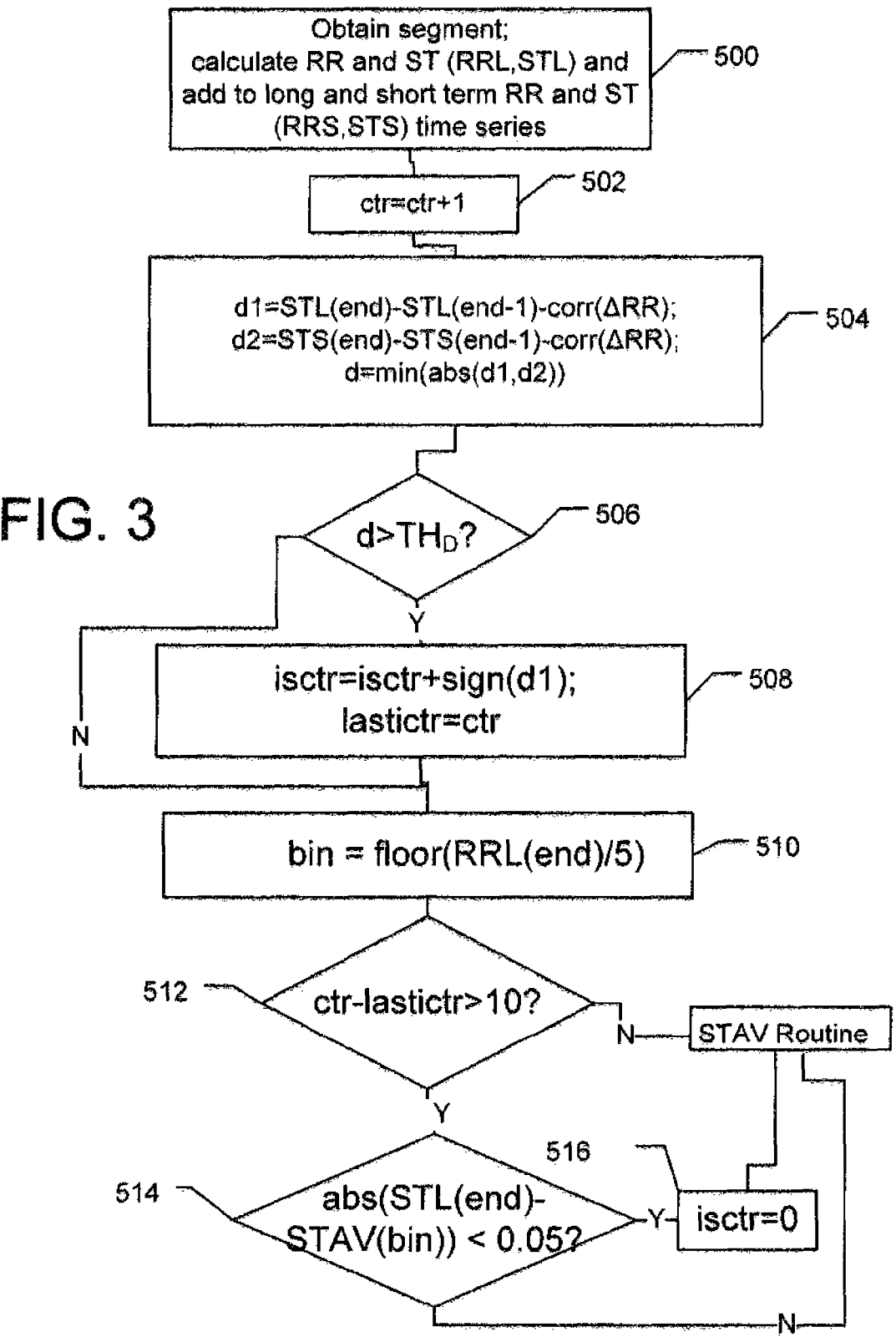
FIG. 3 is a flowchart of a routine that tracks the changes in the ST deviation over time.

FIG. 3 is a flowchart of a routine that tracks the changes in the ST deviation over time. (The parameter tracking scheme shown in FIG. 3 and the other figures will be described with reference to ST deviation but it will be appreciated that the scheme may be applied to tracking other parameters, such as QT interval, QRS duration etc.) Changes in ST deviation are tracked by selectively incrementing or decrementing an integer counter, termed "isctr". In one embodiment, the isctr is incremented only when changes in ST deviation are above a minimum threshold. In another embodiment the isctr is incremented by different amounts as the changes in ST deviation fall within different ranges. In this latter case, the ranges can be set for the patient or population ranges may be used. In a further embodiment more two or more isctr counters can be used and these may be defined with different minimum thresholds, and their results can be combined using "and", or "or" logic.

Changes in isctr are a non-linear function of changes in the ST time series, where the non-linear function is chosen so that the isctr is configured to reach large (absolute) values only when the ST time series has a ramp-like shape.

If an isctr becomes larger (positive or negative) than a defined isctr threshold, then it is likely an acute ischemic event is occurring. In the embodiment described, parameters are chosen to track an acute event; the parameters may be modified to track longer term cardiac events associated with a variety of pathologies such as pericarditis. In one embodiment the isctr is adjusted by subtracting a specified "counter decrement" value periodically until a value of zero is reached. In this manner, if a number of counter increments occur within a selected time, then the counter value will exceed a selected threshold. Counters that track slower events can be defined by assigning relatively smaller "counter decrement" values. Additionally, the counter decrement values may be programmably adjusted.

In block 500, a segment (e.g. 10 seconds) of ECG data is acquired. The segment is examined to determine whether there are enough "good" beats (e.g. non-noisy, sinus rhythm beats); checking for "good" beats will be described more completely with respect to FIG. 5. Long and short term RR interval and ST segment time series data are calculated, preferably according to the methods described in FIG. 5 and in U.S. patent applications, each assigned to the assignee of this invention "Heart Rate Correction System and Methods for the Detection of Cardiac Events" by Hopenfeld, filed August 2009, Ser. No. 12/461,442 ("Heart Rate Correction Application"), and Waveform Feature Value Averaging System and Methods for the Detection of Cardiac Events, filed 9/2007, Ser. No. 11/898,673 by Hopenfeld ("Averaging Application").

In block 502, a variable which serves as counter "ctr", which simply tracks the number of incoming segments, is incremented. In block 504, in the currently illustrated embodiment, the routine calculates the difference in ST deviation between the current data sample and a prior reference, which here is the current segment and the prior segment. More exactly, the difference in the ST deviation is based on the difference between adjacent points in the ST time series (STL or STS), which are filtered versions of the raw ST time series. As is described in the Heart Rate Correction Application, the long term filtered ST time series (STL) can change gradually over time after there has been an abrupt change (e.g. caused by an axis shift) in the raw ST time series, oven though the raw ST time series is actually not changing much. To handle this situation, a short time ST time series (STS) is also calculated, and the actual change in ST deviation (d) is taken to be the smaller of the change in the STS or STL time series, d1 and d2 respectively.

Finally, again as described in the Heart Rate Correction Application, changes in RR interval (ΔRR) cause normal changes in ST deviation, with shorter RR intervals often being characterized by larger ST deviation values. Because the goal of an ischemia detection device is to track abnormal changes in ST deviation, the normal expected ST deviation corr(ΔRR), associated with a change in RR interval ΔRR, is subtracted from the ST time series changes (d1 and d2). The ΔRR values can be calculated for both the long term and short term filtered RR time series. The corr(ΔRR) value can be selected from a lookup table or can be computed based upon an equation and it should be noted that a change from 120 to 100, may have a different corr($\Delta RR$) than a change from 100 to 80 although the change is 20 in both cases.

Block 506 determines whether d exceeds a threshold $TH_D$. The best value of $TH_D$ will depend on a number of factors. If it is desired to detect a change of at least 15% in ST deviation (expressed as a percentage of QRS height) over 3 minutes, a percentage change which seems reasonable based on ECG measurements recorded during balloon angioplasty procedures on human coronary arteries, and if 1 10-second electrogram segment is acquired every 30 seconds, then $TH_D$ should be somewhat less than 0.025/segment (=0.15/6 segments). If adaptive segment processing is employed, so that the time between segments is variable, then $TH_D$ should be adjusted accordingly, If d exceeds a threshold $TH_D$, block 506 passes control to block 508, which increments or decrements the ischemia counter (isctr) according to whether the ST time series change is positive or negative, and also sets a variable, lastictr, to the current ctr value. If adaptive segment processing is employed, so that the time between segments is variable, then isctr should be increased/decreased according to the time between segments. For example, if it has been 90 seconds between segments, isctr may be increased/decreased by 3, whereas if it has been 30 seconds between segments, isctr may be increased/decreased by 1. To more heavily weight smaller, more consistent changes, the increase/decrease in isctr may be a nonlinear function of the time between segments. Continuing with the above example, if it has been 90 seconds between segments, isctr may be increased/decreased by 2 instead of 3.

The variable lastictr, as will be described below with regard to block 512, is used to determine whether "a long time" has elapsed since the last increment to isctr.

In an alternate embodiment, isctr is increased/decreased according to the magnitude of d, with larger values of d result in larger changes to isctr according to a linear or non-linear function.

From either block 506 or block 508, control passes to block 510, which calculates the current RR interval range. (The factor of 5 in the denominator results in RR interval ranges/bins that are 5 units wide.) As will be described more fully with reference to FIG. 4, RR intervals are divided into a number of non-overlapping ranges (bins), and a measure of the average ST deviation, and the maximum and minimum differences from that average, is calculated.

From block 510, control passes to block 512, which checks how long it has been (i.e., how many segments have been collected) since the ischemia counter (isctr) has been updated by computing the quantity ctr-lastictr. If it has been a relatively long time since isctr has been updated, then it may be appropriate to reset isctr to 0, or to otherwise decrement the isctr value, in order to prevent random drifts which occur in the electrogram data from pushing isctr to large (absolute) values. Thus, in block 514, if the current ST deviation value (STL(end)) is relatively close to an expected value such as the average value for the current RR interval range (STAV(bin)), then the ischemia counter is reset in block 516. The ST deviation values, such as STL(end) and STAV(bin), are preferably expressed as a percentage of a measure which may often be the average long term QRS amplitude; see e.g. block 606 in FIG. 5.

In an alternate embodiment, the absolute value of isctr is decreased if the magnitude of d does not exceed $TH_D$, unless the isctr is already 0

Figure 4:
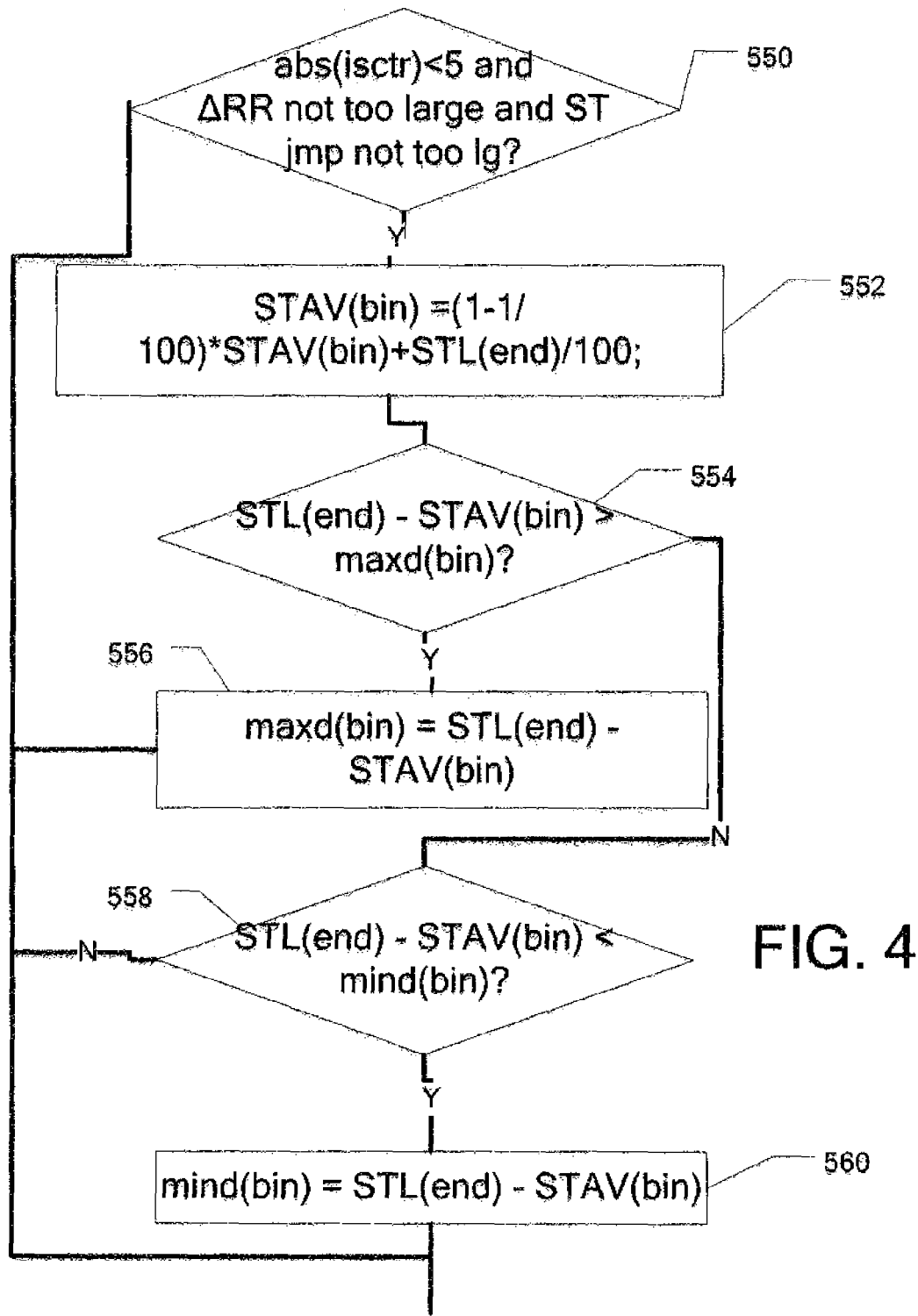
FIG. 4 is a flowchart of the routine that tracks the average ST deviation, and the maximum and minimum differences from that average, for a number of RR interval bins.

If it has not been too long since the last isctr increment, then block 512 passes control to the STAV routine shown in FIG. 4, Additionally, if the current ST value (STL(end)) is not close to the average value (STAV(bin)), then isctr is not reset, and control passes to the STAV routine of FIG. 4. Not resetting isctr, even if it has been a long time since isctr was updated, allows isctr to track situations where the ST level changes in one direction but not smoothly (e.g., a rapid increase is followed by a plateau which is followed by another rapid increase).

FIG. 4 shows the routine that tracks the average ST deviation, and the maximum and minimum differences from that average, for a number of RR interval bins. In block 550, the routine determines whether to update the current RR interval bin by checking the value of isctr. If isctr is too large, then an acute ischemic event may be occurring and it is not desirable to update the bin to include this abnormal ST data. Also, if a rapid change in heart rate has just occurred, or has occurred recently, then the current ST value for the given RR bin (or RRS or RRL bin) may be quite different than the normal ST values for that bin. The Heart Rate Correction Application describes methods for determining when $\Delta RR$ is sufficiently large to determine that a given ST level is not representative of the current RR interval. Finally, in case that non-sinus or very noisy beats somehow passed through all of the foregoing detection criteria, the current RR interval bin is not updated if the jump in the ST value of the current segment (compared to STL(end)) is too large.

If isctr and $\Delta RR$ are not too large, block 550 passes control to block 552, which updates the average value for the bin (STAV(bin)) by computing an exponential average. The factor of 100, as will the the other factors in FIGS. 3-5, will generally be implementation dependent. Control passes to block 554, which checks whether the difference between the current ST level (STL(end)) and STAV(bin) is greater than the previous maximum difference for the bin (or to a default value in the case where the algorithm has recently been started or reset). If so, the new maximum (maxd(bin)) is set to STL(end)–STAV(bin). Otherwise, control passes to block 558; blocks 558 and 560 are analogous to blocks 554 and 556 except that the former pertain to the minimum difference between STL(end) and STAV(bin).

In addition to tracking the average, maximum and minimum ST deviations, the average change from the average could be tracked by maintaining an exponential average of the absolute value of the difference between the current segment's ST deviation and the average ST deviation. Larger values of this average change metric could suggest a pathology (e.g. pericarditis, chronic ischemia) with a longer time frame than acute ischemia. Indeed, the exponential average factors used to compute the average value and the average change could be tuned according to the time frames of various pathologies. Also, the update frequency for the average change metric could be decreased (e.g. updates once per hour) to track longer term trends, in which case the exponential average factor would have to be adjusted accordingly (e.g., if updates are made once/hour, an exponential average factor of 1/24 would result in an exponential average that is approximately equivalent to a moving average for a day for relatively smooth trends.)

Figure 5:
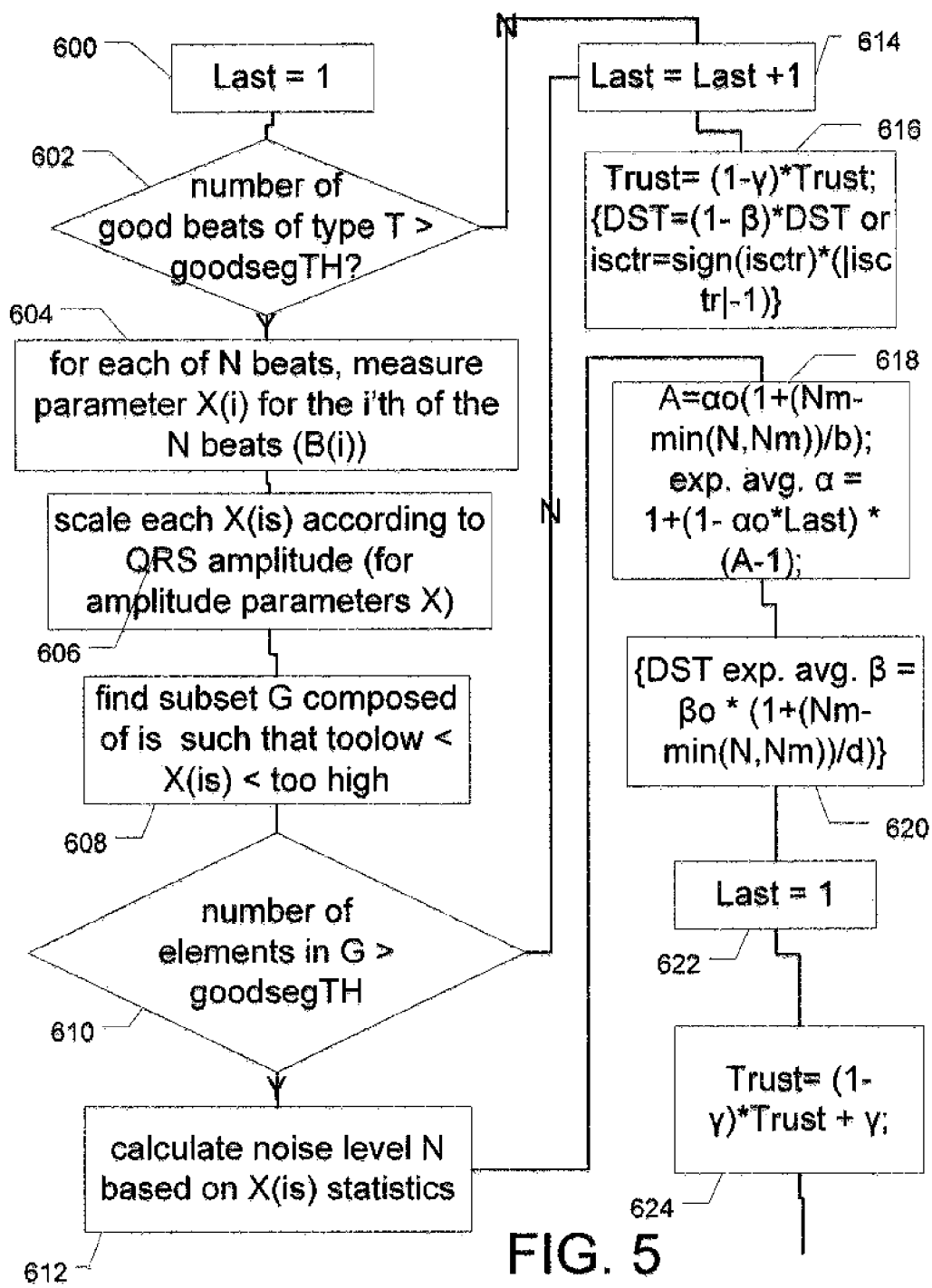
FIG. 5 is a flowchart of a routine that handles cases in which a relatively long gap in time may have elapsed between segments that contain good data for a certain type of beat (e.g. sinus rhythm beats or paced beats).

FIG. 5 is a routine that handles cases in which a relatively long gap in time may have elapsed between segments that contain "good data" for a certain type of beat (e.g. sinus rhythm beats or paced beats). These gaps between segments may be caused by a number of factors such as bursts of noise or long runs of other types of beats such as non-sinus beats. In one embodiment of the present invention which is useful in conjunction with a pacemaker device, the ST levels for both paced beats and sinus beats are separately maintained. Since these two types of beats may occur in long runs, it is desirable to alter ischemia tracking metrics (e.g. the isctr described with reference to FIG. 3) according to the time that has elapsed between segments that contain good beats of the specified type (either sinus or paced).

In block 600, a counter Last is initialized to 1. This counter tracks the number of segments between segments containing "good" data for a certain beat type (T). In block 602, the number of beats of type T is determined, If there are a sufficient number of good beats of type T, control passes from block 602 to 604, which measures a parameter "X" the ST deviation for each beat of type T. In block 606, in order to address fluctuations in signal amplitude, this deviation is scaled by an average QRS amplitude factor which can be computed using prior or current data for that beat type. In block 608, beats with ST deviations that are above and below certain "noise-rejection" thresholds are removed, resulting in a subset G of good beats with accepted ST deviation values. These noise threshold values may be adjusted adaptively according to whether an acute ischemic event is more likely to be measured from the current data; for example, if isctr is above a selected positive threshold, then the positive noise threshold for ST deviation may be increased. if the number of elements in G is large enough (preferably >=4 beats), then block 610 passes control to block 612, which calculates the ST noise level for the good beats G. In an alternative embodiment, block 610 examines whether a variable (badbtctr), which is implemented as a "leaky bucket" that tracks bad beats over all segments (not just the current segment), exceeds a threshold. The leaky bucket embodiment is described with reference to FIGS. 15a and 15b.

The noise level N may be calculated as the standard deviation of the ST deviations, or, to reduce battery consumption, the noise level may be set equal to the average absolute value difference between the ST deviations and their mean, which will be referred to as $ST_{mn}$. Alternatively, the noise level could be determined according to the number of zero crossings of the first derivative of the signal.

In block 618, the exponential average factor a used to filter the ST deviation time series (e.g. to obtain the STL time series described with reference to FIG. 3) is computed. (E.g. STL(end)=$(1-\alpha)$*STL(end-1)+$\alpha$*$ST_{mn}$). If the noise N is low, the factor $\alpha$ is preferably increased to add weight to the current measurement. The temporary, noise scaled exponential average will be referred to as A.

If a very long time has elapsed since the last segment with good beats of type T (i.e. Last is large), then the previous value of the ST time series (e.g. STL(end)) should not be used to compute the current ST time series value. For example, if STL(end) was last updated 5 minutes ago, the current ST value is likely so far different that it does not make sense to consider STL(end) when calculating the current STL value; in other words, it is best to simply start over, which means that a should be reset to 1 so that the new STL(end)=$ST_{mn}$. More generally, a should be increased as Last increases, preferably according to the same rate corresponding to the baseline $\alpha_o$. Formally, it would make sense to increase a according to exp($-\alpha_o$*Last) but this may be approximated by $1-\alpha_o$*Last, which has the advantage of increasing a relatively more rapidly at relatively large values of Last. The equation $\alpha=1+(1-\alpha_o$*Last)*(A-1) results in an $\alpha$ approaching 1 as Last gets large and results in an a that approaches A as Last approaches 0. In the embodiment shown in FIG. 5, the minimum value of Last is 1.

In block 620, if an ST time series slope factor (DST) is computed (see the Heart Rate Correction Application and the Averaging Application), then the exponential average for the slope factor is preferably noise weighted. In block 622, Last is set equal to 1 to indicate the current segment involved an update to the ST time series. Finally, in block 624, a factor (Trust) is updated according to an exponential average; Trust serves to gauge the confidence level in the current ST value by tracking the relative frequency of segments with acceptable beat types. If a long time has elapsed since the last ST update, this relative frequency (with frequency here being a time based measure) is low, and therefore Trust should be low, and a number of good segments with beats of type T should have to occur before Trust becomes high. These Trust characteristics are implemented by the combination of block 624, which increases Trust after a good segment, and block 616, which decreases Trust after each "bad" segment.

In an alternative embodiment, "good" segments are further characterized according to noise level, so that in block 624 Trust is increased by less than $\gamma$. In particular, according to this alternative embodiment, Trust=$(1-\gamma)$*Trust+max(0, (No-N)/No)*$\gamma$; where N is the noise level of the current segment and No is a maximum noise cutoff parameter.

In yet another alternative embodiment, Trust may be set equal to a variable (badbtctr), which is implemented as a "leaky bucket" that tracks bad beats over all segments, as will be described with reference to FIGS. 15a and 15b.

If for whatever reason the current segment does not contain a sufficient number of good beats of type T, control (from block 602 or 610) passes to block 614, which increments Last and passes control to block 616. As mentioned, block 616 decreases Trust after a "bad" segment. Block 616 also decreases DST or the isctr, whichever is used to track temporal changes in ST levels. In the embodiment shown, isctr is decreased (in absolute terms) by one unit; in an alternative embodiment, isctr is decreased by less than one unit. The amount to decrease isctr could be made adaptive according to whether another beat type has an isctr that is currently being incremented. For example, if there are no sinus beats in a current segment because all beats are paced, and the paced beats are experiencing an ST level change such that the paced beat isctr is currently being increased (in absolute terms), the sinus isctr may be decreased by less than one unit (or not decreased at all).

These temporal trackers, which in some sense represent a rate of change of the ST level, are decreased based on the assumptions that no change has occurred in the parameter. Of course, a change may have occurred, but there is no way of knowing that, so reducing these temporal trackers will tend to reduce false positive cardiac event detections.

Figure 6:
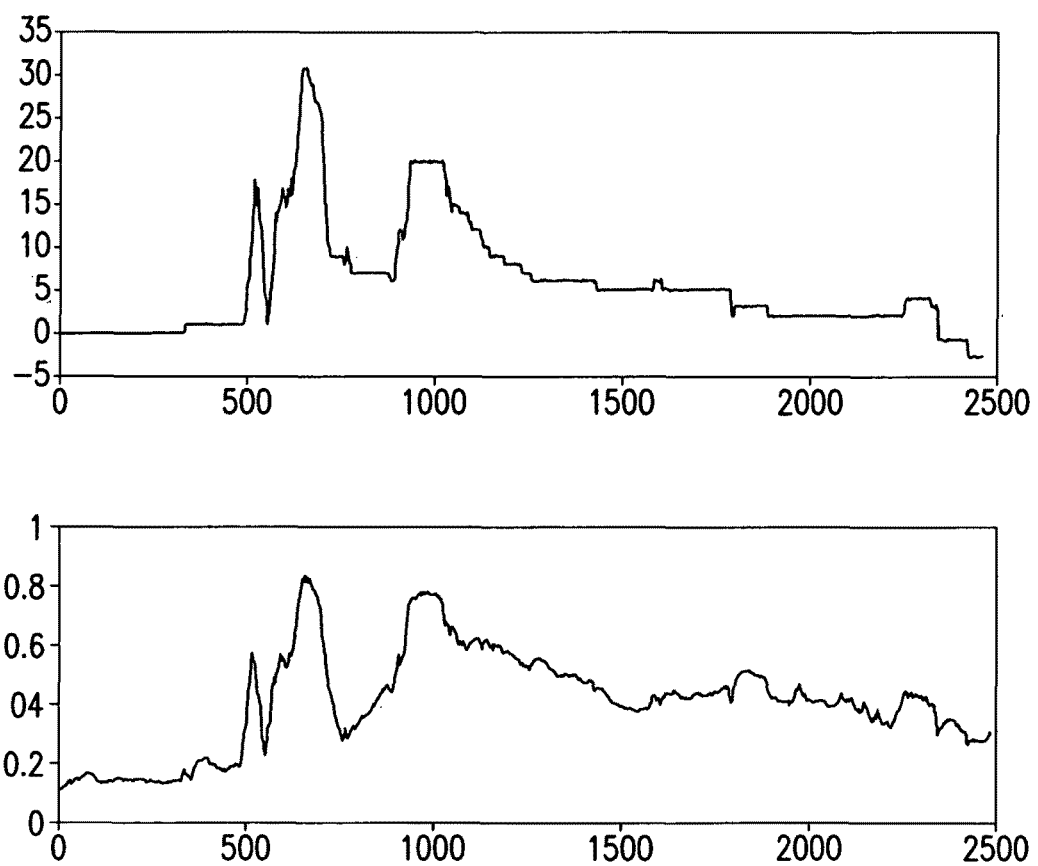
FIG. 6 shows plots of variables calculated according to the routine in FIG. 3, as applied to data associated with a subcutaneous lead in the setting of a porcine coronary occlusion.

FIG. 6 contains a top panel which shows time series values which are output from an ischemia counter (isctr; FIG. 3) which is calculated upon data associated with a subcutaneous lead in the setting of a porcine coronary occlusion. The bottom panel shows the ST time series and the time panel shows isctr, which mirrors the morphology of the ST time series.

Figure 7:
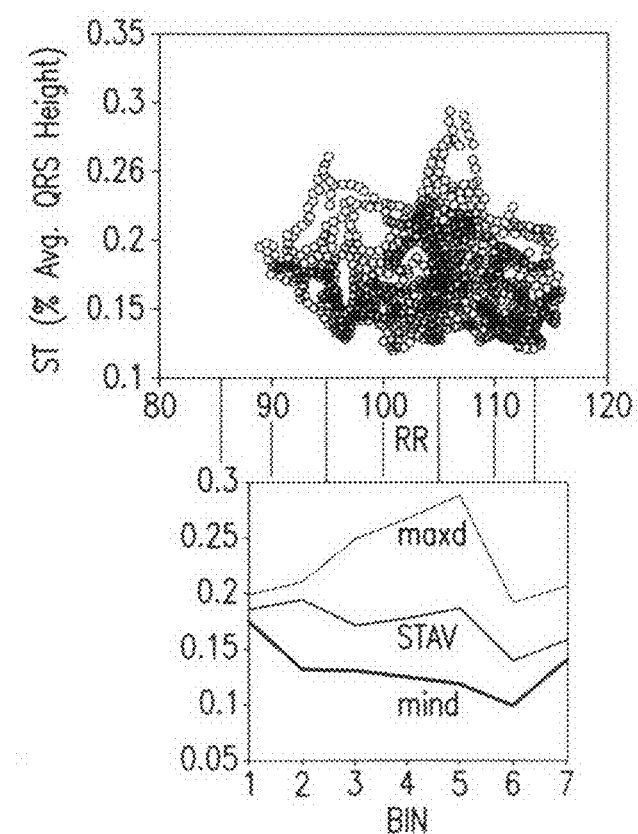
FIG. 7 shows plots of variables calculated according to the routine in FIG. 4, as applied to data associated with a subcutaneous lead in the setting of a porcine coronary occlusion.

FIG. 7 shows the average ST and maximum and minimum deviations from that average over a number of heart rate bins, as computed by the routine shown in FIG. 4. The ST data was gathered from a subcutaneous lead in a pig.

Figure 8:
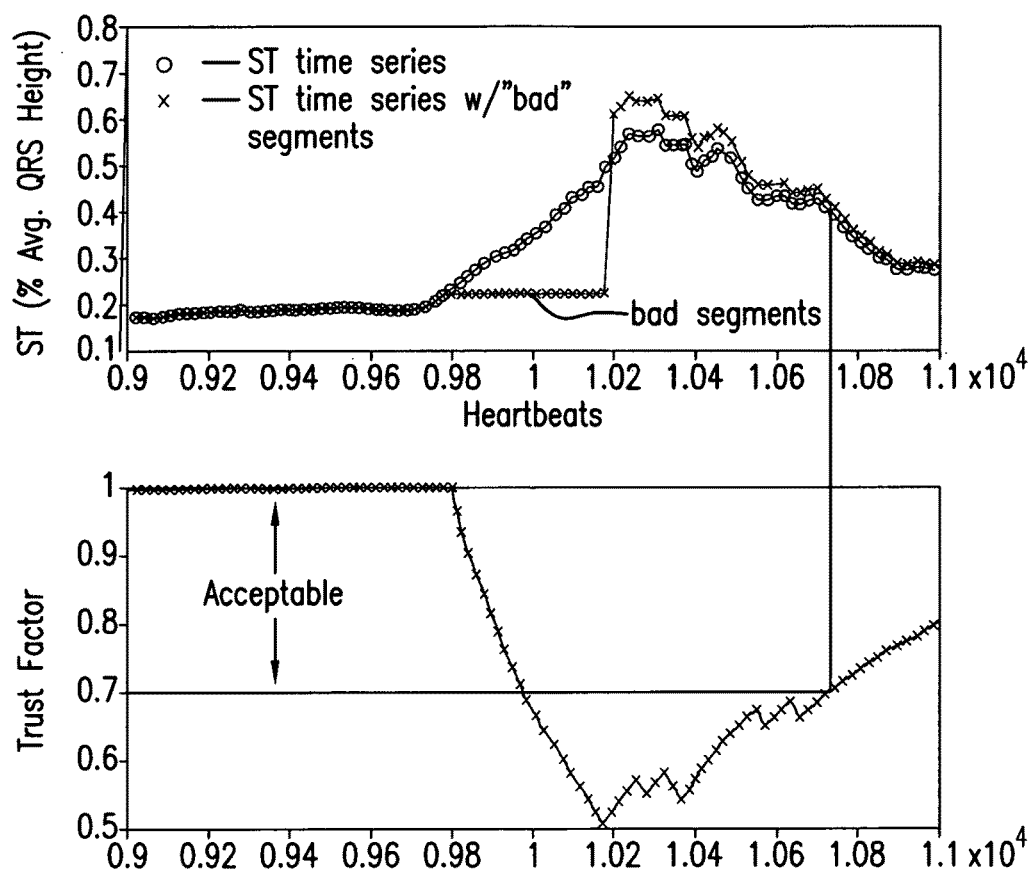
FIGS. 8 and 9 shows plots of variables calculated according to the routine in FIG. 5, as applied to data associated with a subcutaneous lead in the setting of a porcine coronary occlusion.

FIG. 8 illustrates the operation of the Trust factor (FIG. 5) in the context of subset of the data shown in FIG. 6 lower pannel. A number of actual data segments were artificially made very noisy by digitally adding Gaussian noise to the signal (labeled "bad segments" in the figure and spanning from heartbeat 9800 to 1200). The Trust factor (lower panel) according dropped from 1 to 0.5, where 0.7 is the minimum level required by the trust variable for data to be accepted. The Trust factor began to rise only after the resumption of the appearance of good segments. After the bad segments the ST time series containing these segments (X's in the top figure) converged to the "true" ST time series after about 400 heartbeats or roughly 40 additional segments of data were collected. This is around the same time that the trust factor returned to a level that the ST data would again be allowed to enter the accepted dataset, showing evidence that the algorithm worked as intended in this case.

Figure 9:
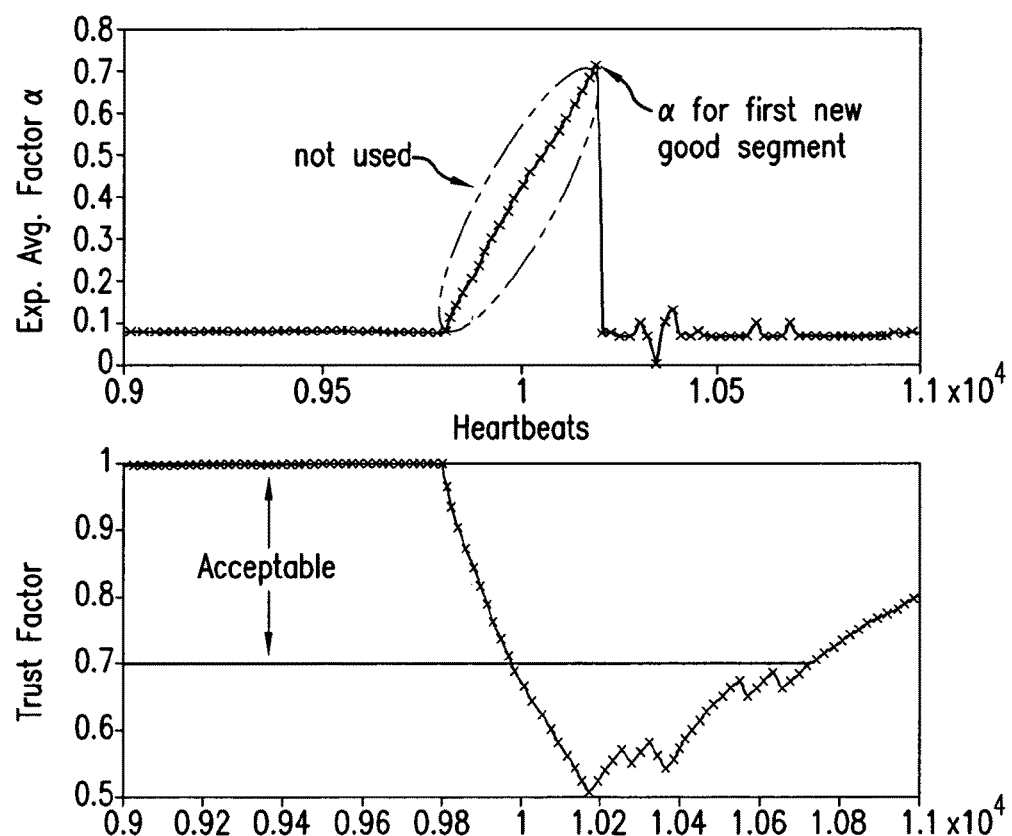

FIG. 9 shows the exponential average factor a associated with the scenario shown in FIG. 8. The average factor a increases (but is not used) as the number of bad segments increases. This "increase" is not actually calculated in FIG. 5 but is shown here for illustrative purposes; α is actually calculated only after the resumption of good segments which here occurs at after beat number 17,500 ($1.75 \times 10^4$. The lower panel again shows the same Trust factor plot that was shown in the bottom panel of FIG. 8.

FIGS. 10a, 10b and 11 are tables that show various combinations of parameter/tracker values that will trigger a cardiac event detection. The table in FIG. 10a applies to cardiac event detection based on analysis of a single beat type (e.g. sinus rhythm). Cardiac event detection will occur if all of the conditions across any of the rows are satisfied. For example, an event will be triggered if the conditions in row 1 are satisfied, namely that the time series tracker (isctr or DST) exceeds a threshold and the absolute ST level exceeds a threshold. An event will also be triggered if the condition in row 2 is satisfied, namely that the ST level exceeds a higher threshold (maxd(bin)+0.2) than the threshold that applies to absolute ST in row 1 (maxd(bin)+0.1). (All numbers without units in the tables are fractions of QRS amplitude; e.g., 0.1 means 10% of QRS amplitude).

FIG. 10b shows a detection scheme that combines both ST segment changes and the presence of irregular rhythms.

With regard to QRS duration increases, detection can only occur if the QRS duration increase has been relatively smooth. If a QRS duration increase has been abrupt, then the beats with these long QRS durations will rejected (not classified as sinus beats or whatever other types of beats are being tracked) according to the routine described with reference to FIG. 11, which examines QRS duration to determine whether a beat is a sinus (or other type of tracked) beat. If the QRS duration change has occurred relatively smoothly, however, then the QRS duration test (FIG. 12) will not be applied to determine whether the beat is a sinus beat, so that sinus beats with long QRS durations can be detected.

At a sampling rate of 200 Hz, a QRS duration increase of 15 ms corresponds to an increase in QRS duration of 3 samples. Because of the discrete nature of the sampling process, raw QRS durations will not increase smoothly. For example, an increase from 14 samples to 15 samples may appear something like (14 14 14 15 14 15 15 14 14 15 15 15). However, exponential averaging (or some other type of filtering) will help to create a smooth trend from this type of data.

FIG. 11 is a table for detecting a cardiac event when two beat types, e.g. paced beats and sinus beats, or beats from two different leads, are being analyzed. The entries in the table are based on the assumption that the polarity of the ST changes associated with paced and sinus beats are known to be in the same direction, A more general embodiment that handles different types of beats (e.g. sinus beats and junctional beats) or lead setups, need not incorporate this assumption; a cardiac event could be triggered based on combinations of the absolute values of the respective tracker and ST levels. For example, an event could be triggered if |sinus isctr|>TH1 and |non-sinus isctr|>TH2.

Figure 13:
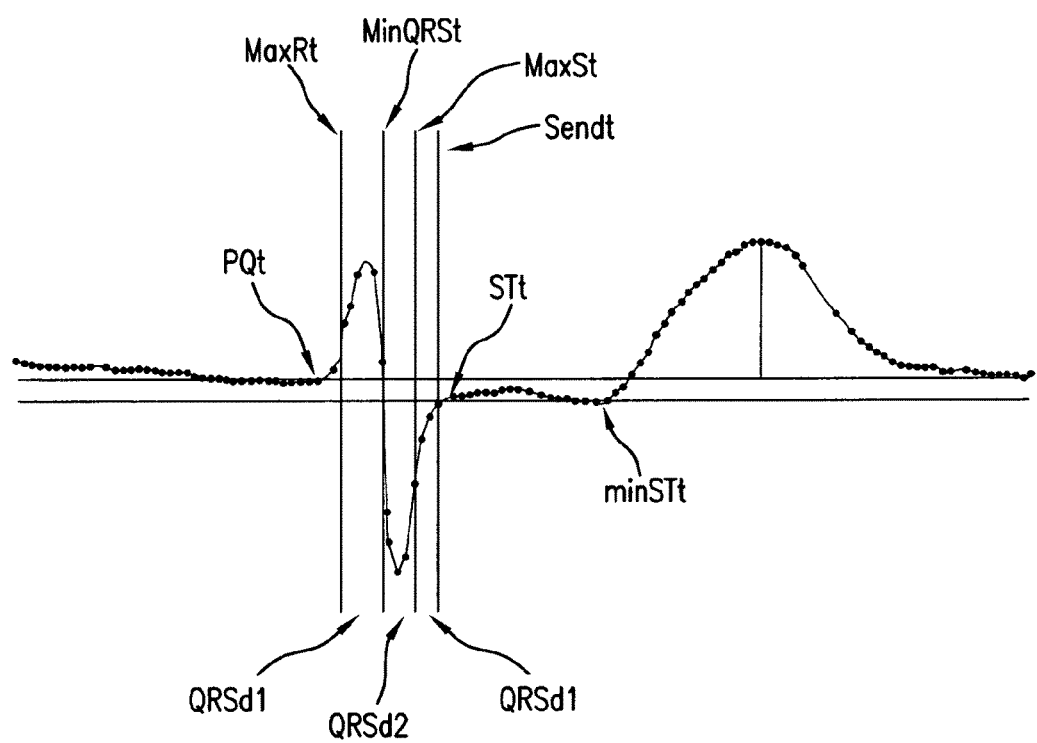
FIG. 13 shows how various cardiac parameters are defined by labeling those parameters on electrocardiograms for a single heart beat.

FIG. 12 is a flew chart of a routine that determines whether a particular beat is classified as a particular beat type (e.g. sinus rhythm, which for ease of illustration will be used as the desired beat type in the discussion hereafter.) This determination is based upon various beat type parameters (BTP's), listed in block 698 and shown graphically in FIG. 13, that are combined. In FIG. 13, voltage based variables are appended with the "t" to denote the sample (or region of samples) which is used to define to the voltage based variable in question. For example, the PQ voltage is defined as the voltage of the signal at time (sample) PQt. The signal will be denoted as D, so that the PQ voltage is D(PQt). MaxR, MinQRS and MaxS are the times associated with maximum absolute slope values during the upstroke of the R wave, downstroke and upstroke of the S wave respectively. (The minimum QRS slope, MinQRS, is a negative quantity. Slope is preferably calculated in the manner described with reference to FIGS. 14a-14d.) ST deviation (STdev) is defined as D(STt)-D(PQt). QRS duration components QRSd1, QRSd2 and QRSd3 are defined as MinQRSt-MaxRt, MaxSt-MinQRSt and Sendt-MaxSt, respectively.

The acceptable BTP parameter ranges for sinus rhythm will depend on a particular lead. For example, lead 15 (FIG. 1) would typically result in a QRS morphology as shown in FIG. 13, which also shows how various BTP's (or constituents thereof) are defined. In this case, a non-sinus beat is identified if:

MaxR/MinQRS is less than threshold and STdev is small or negative; or

QRSt1, QRSt2, or QRSt3 are greater than or less than specified amounts

The first criterion involves checking whether the R wave is too big by computing the ratio of slopes MaxR/MinQRS. (Alternatively, the R/S amplitude could be checked.) If so, the cause is a non-sinus beat, unless the relatively large R wave results from massive PQ segment depression caused by an anterior ST elevation event, in which ease the ST deviation (STdev) for the beat will be positive (in a lead positioned such as lead 15 in FIG. 1). If such ST elevation is absent bit the R wave is large, then a non-sinus beat is likely.

In FIG. 12, block 700 checks whether any BTP's are gradually changing for sinus beats by examining a counter analogous to isctr or an exponential average analogous to DST for the BTP in question. If so, then an acute event may be occurring that alters the morphology of the sinus QRS. To avoid incorrectly characterizing sinus beats as non-sinus, in block 702, the BTP's that are gradually changing are removed from the beat tests or entire beat tests are removed. For example, if the PQ segment is gradually becoming more negative due to a worsening anterior ST elevation event, which would be associated with a gradual increase in the R wave height (or MaxR/MinQRS ratio), then all tests based on R wave height are not performed, if the current segment's R wave is consistent with the trend.

Patients that have experienced an anteroseptal MI may not have any R waves in lead 15. Apart from these patients, an additional test for capturing non-sinus beats would be to require that MaxR/MinQRS exceeds a minimum specified amount.

Checking for P waves requires additional computational resources and is dependent on a lead that generally registers robust P waves. If P wave checking is performed, however, the resulting P wave parameters can serve as an additional criterion for catching non-sinus beats. For example, if the maximum amplitude of the signal within a heart rate adjusted window preceding the QRS onset point (PQt in FIG. 13) does not exceed a threshold, the beat may be characterized as non-sinus. Finally, block 704 performs the above mentioned tests to detect non-sinus beats.

Figure 17:
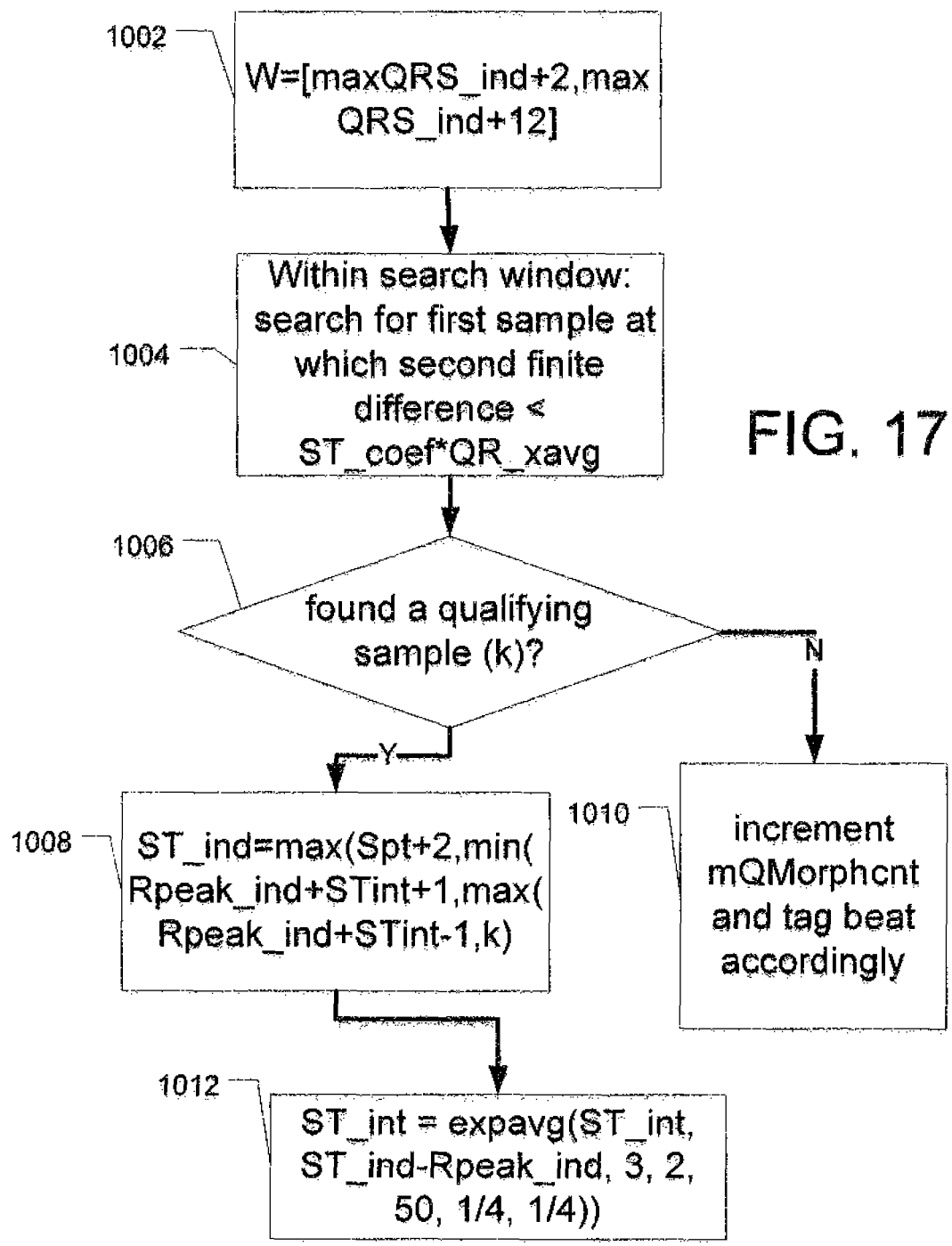
FIG. 17 is a flow chart of a routine that determines the location of ST points.

FIGS. 14a-14d, along with FIG. 17, are collectively a flow chart of a routine that finds the location of the samples that are used to determine ST deviation. Roughly, ST deviation is a function of the difference in signal amplitude between the ST and PQ segments of a heart beat. The flowchart will be described with respect to finding the location within a beat at which to measure PQ segment amplitude. Analogous steps may be performed to find an appropriate ST segment measurement point. However, the preferred embodiment for finding ST segment measurement points will be described with reference to FIG. 17.

The flowcharts described below incorporate the following definitions: D[i] is the value at point/sample i within a segment; and S[i] is the slope at point i, =D[i+3]+2*D[i+2]+D[i+1]D[i−1]2*D[i−2]D[i−3]. The exponential average of a variable (V) is expavg(V, Δ, α, min, max, mindelt, maxdelt), which means that the variable V is updated by the current value Δ, with an update weighting $½^α$, subject to constraints on the maximum and minimum allowable value for the variable and changes in that variable, Ignoring the constraints, expavg(V, Δ, α, [ ], [ ], [ ], [ ]) is V(j+1)=$((2^α−1)*V(j)+Δ)/2^α$.

The method described in FIGS. 14a-14d determines PQ and ST points only for normal beats. Abnormal beats are detected and noted but their ST deviation $^{is}$ not computed, A normal beat for a particular lead is dependent on the orientation of that lead with respect to the heart and other patient specific factors. In the method described in FIGS. 14a-14d, a normal beat is assumed to have a significant downstroke, i.e. a normal beat does not include a QRS morphology characterized by a single large upstroke followed by a single large downstroke.

Blocks 800 through 822 (FIG. 14a, 14b, 14c) are performed iteratively for each beat in a segment of electrocardiogram data, Before the PQ/ST location diction is invoked, a segment of data has been analyzed to detect beats, preferably by a routine based on the slope based scheme described in U.S. patent application Ser. No. 12/232,281, entitled "Methods and Apparatus for Detecting Cardiac Events Based on Heart Rate Sensitive Parameters", flied 9/2008, owned by the assignee of the present invention. For each beat, the absolute minimum of the QRS (Rpeak) is located and the location of the preceding positive peak (initpk), if any, is determined. The average RR interval for the segment is computed. Based on the average RR interval, PVC beats are located, tagged, and not included in the segment's ST deviation;. the PQ and ST times are not located for PVC beats.

For each non-PVC beat in the segment, in block 800, the minimum QRS slope (minQRS) is located. Block 802 searches for a positive peak in the slope (rnaxQRS) within a search window located after Rpeak. In particular, the search window begins at 2 samples after Rpeak and ends 12 samples after Rpeak. In the figures, a search window is denoted by W[a,b], where a is the window starting point (sample index integer) and b is the window ending point. The sample index (location) associated with a particular reference point is denoted by appending "_ind" to the particular reference point. For example, the index associated with Rpeak is Rpeak_ind. The preferred window values, and all other time based values associated with FIGS. 14-17, are based on a 200 Hz sampling rate.

If a local peak in the positive slope is found at either end of the purposely too wide search window designated in block 802, block 805 increments the "bad beat counter" labeled as mQMorphent and in block 807 the routine searches for the next beat or the end of the segment. Otherwise, if block 802 has found a local positive slope peak, control transfers to block 803, which checks to see if there is an appropriate decrease in the positive slope after maxQRS. In particular, within W[maxQRS_ind+1, maxQRS_ind+8], the routine searches for the first point where the slope is less than ⅜ of maxQRS. If no such sample can be found, the beat is tagged as irregular, the mQRMorphent is incremented in block 805, and processing continues in block 807. Otherwise, control passes to block 804 in FIG. 14b.

In block 804 (FIG. 14b), the routine determines whether the beat has been classified (by the segment based QRS detection routine) as having an initial positive peak (initpk). If so, in block 806, the PQ search window is set at [initpk_ind−2, initpk_ind−16] so that it precedes the initial peak. Otherwise, in block 808, the initial search window is set at [minQRS_ind−6, minQRS_ind−20] so that it precedes minQRS.

Control from either block 806 or block 808 passes to block 810, which searches for the first of two consecutive samples at which the absolute value of the slope is less than an adaptive threshold, mPQslopeth. The search is performed backwards, starting at the beginning of the search window. (More generally, if W[a,b] is such that a>b, the search in window W is performed backwards.) The slope is preferably an average of values at surrounding samples; in the preferred embodiment, S[i]=D[i+3]+2*D[i+2]+D[i+1]−D[i−1]−2*D[i−2]−D[i−3].

If two consecutive samples are found that satisfy the slope test, then block 812 passes control to block 814 (FIG. 14c), which sets the PQ point as the index of the first of the two consecutive samples.

Returning to block 812 (FIG. 14b), if two consecutive samples that pass the test in block 810 are not found, then block 812 passes control to block 816 (FIG. 14c). Block 816 finds the two consecutive samples with the minimum sum (msl) of absolute values of slope within the search window. Block 816 transfers control to block 818, which checks whether msl is less than a maximum allowable threshold, preferably equal to 8 times (a factor of 2 because msl is a sum of 2 slopes and a factor of 4 to ensure the slope isn't wildly different from the norm) mPQslopeth. If msl is greater than the maximum allowable threshold, the beat is tagged as non-analyzable in block 822. An analyzable beat is one whose ST deviation is computed. In an alternate embodiment, the mQRMorphent is alosincremented. Otherwise, if msl is less than the maximum allowable threshold, the PQ point is set at the first of the two points (msl_ind) and mPQslopeth is updated (increased) based on the value msl.

After all the beats in a segment have been processed, segment based processing resumes in block 824, which checks whether the number of analyzable beats in the segment is greater than two. If so, control passes to block 826 (FIG. 14d), which computes the average PQ slope of the segment (PQslopeThavg) based on the slopes at the PQ points for each analyzable beat in the segment. If the number of analyzable beats in the segment is less than or equal to two, control passes to block 828 (FIG. 14d), which sets PQslopeThavg as the existing PQ slope threshold (mPQslopeTh). From either block 826 or 828, control passes to block 830 (FIG. 144 which computes the outcome of a number of tests that are compounded in block 832 to determine whether to update mPQslopeTh. In particular, blocks 830 and 832 determine that an update should occur in block 834 if: (1) at least 3 beats in the segment are analyzable and either: (2) the average segment RR interval is between ¾ and 3/2 of the previous segment's average RR interval; or (3) mQMorphCnt is less than 2 and the number of PVC's in the segment is less than 2. As will be further described below, the number of analyzable beats is tracked by STDNent in block 858 of FIG. 15a. In an alternate embodiment, the determination whether to update exponential averages is based on a variable, mqmorph (see FIG. 16 and associated discussion) that tracks long term trends in the relative frequency of abnormal beats.

Block 834 updates mPQslopeTh by computing an exponential average based on PQslopeThavg. The updating is performed such that mPQslopeTh can never be less than initPQslopeTh, an empirically determined value, and can never be greater than an empirically determined value, max-PQTH. The initial mPQslopeTh is set at initPQslopeTh.

Figure 14A:
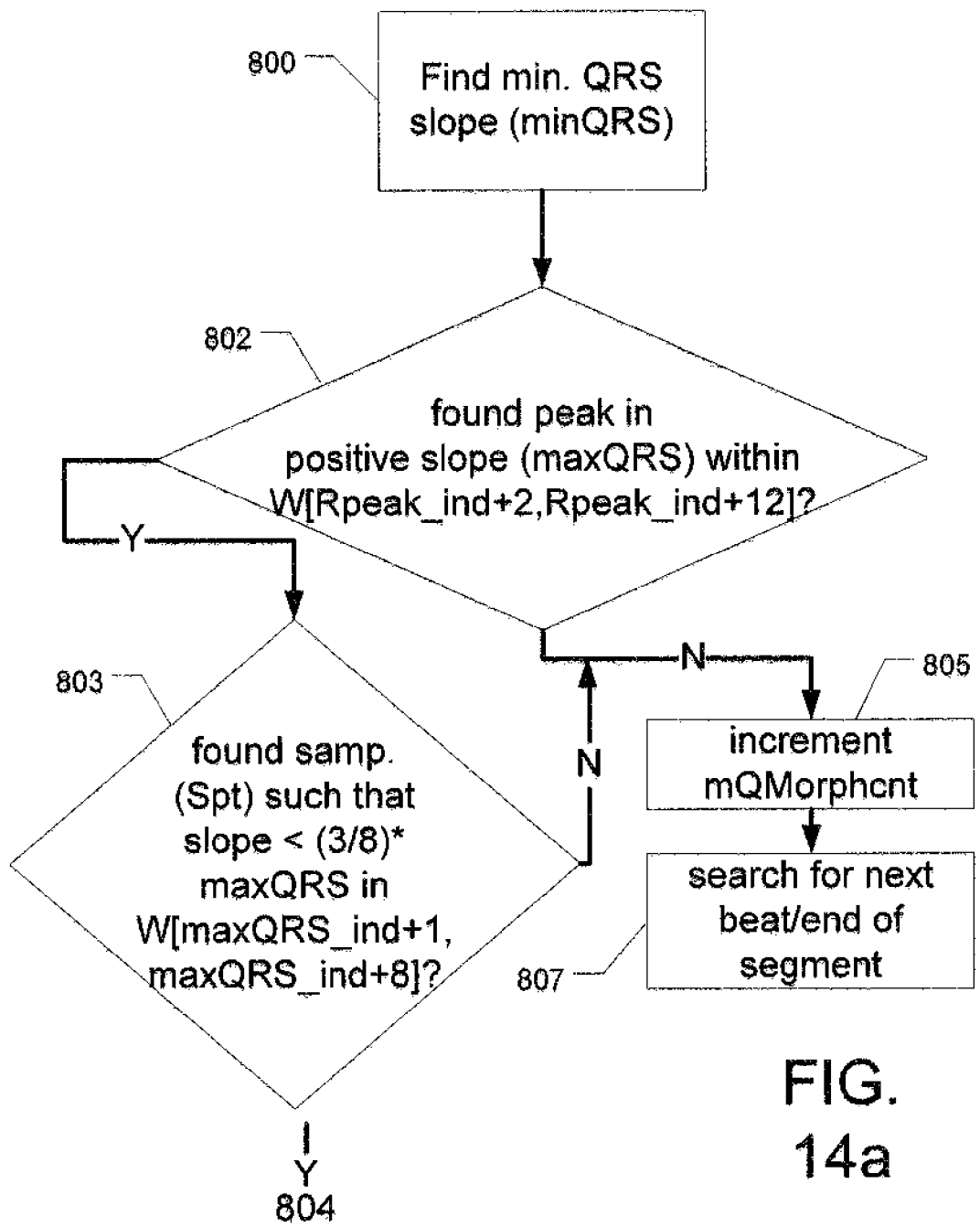
Figure 14B:
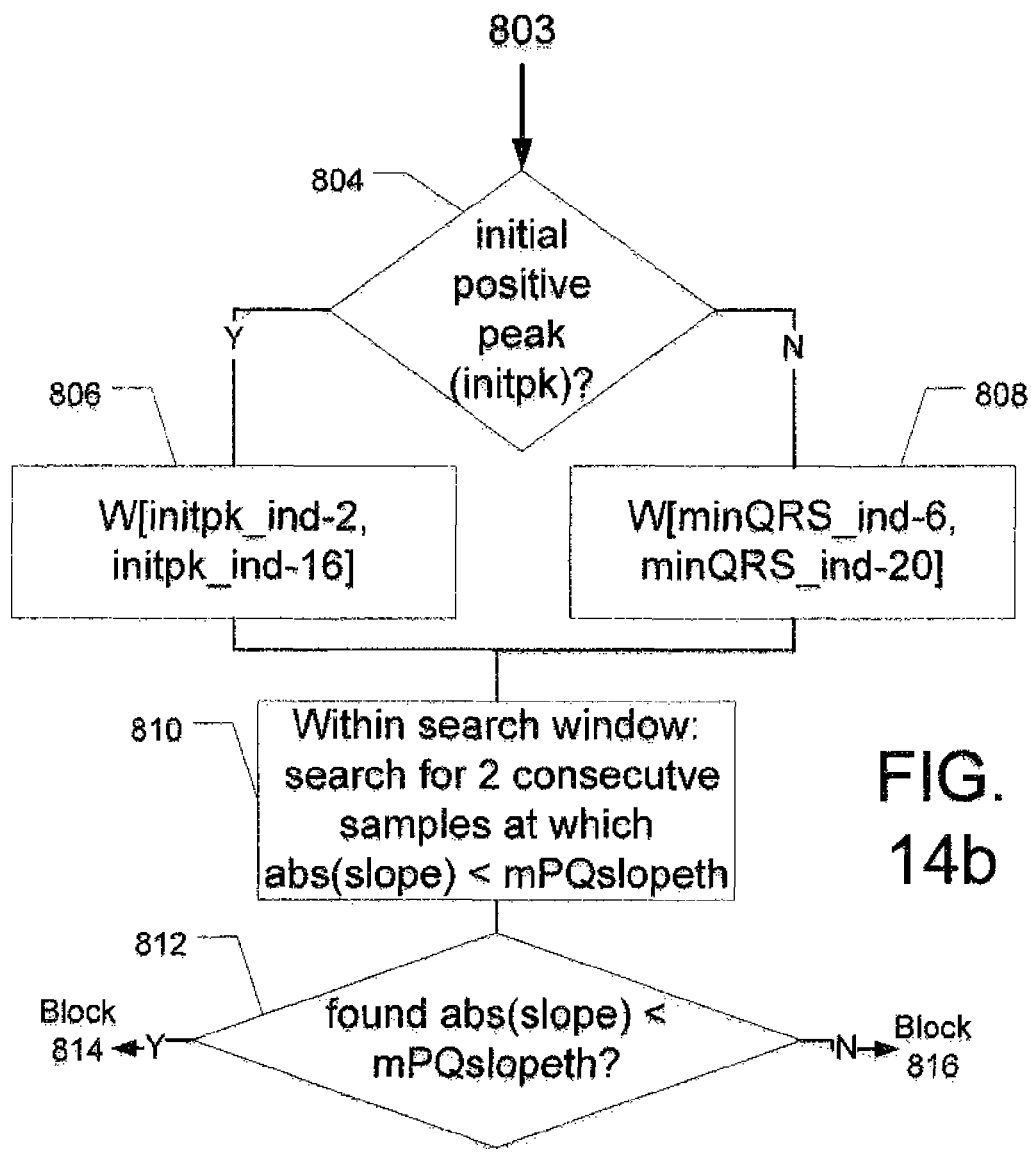
Figure 14D:
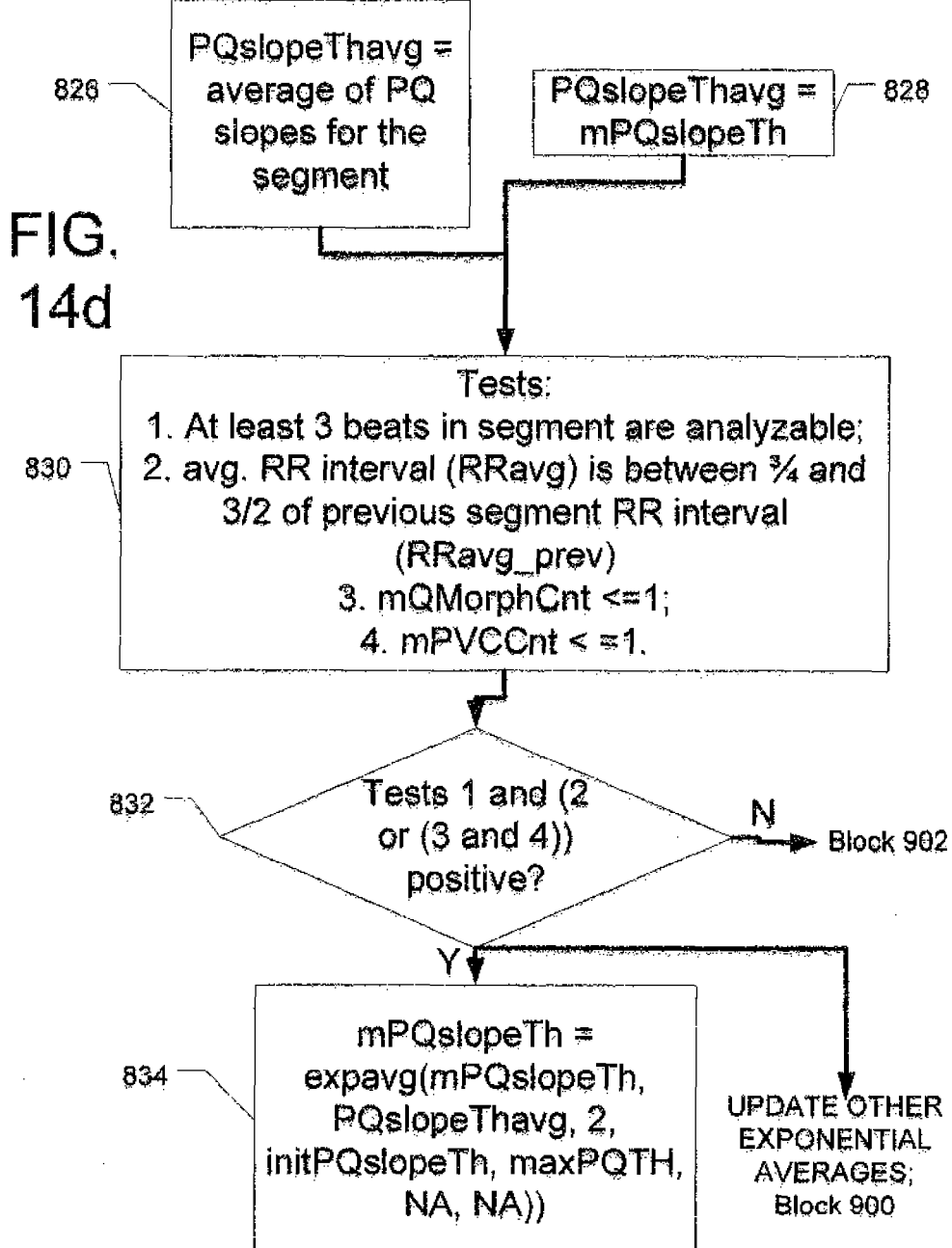
Figure 15A:
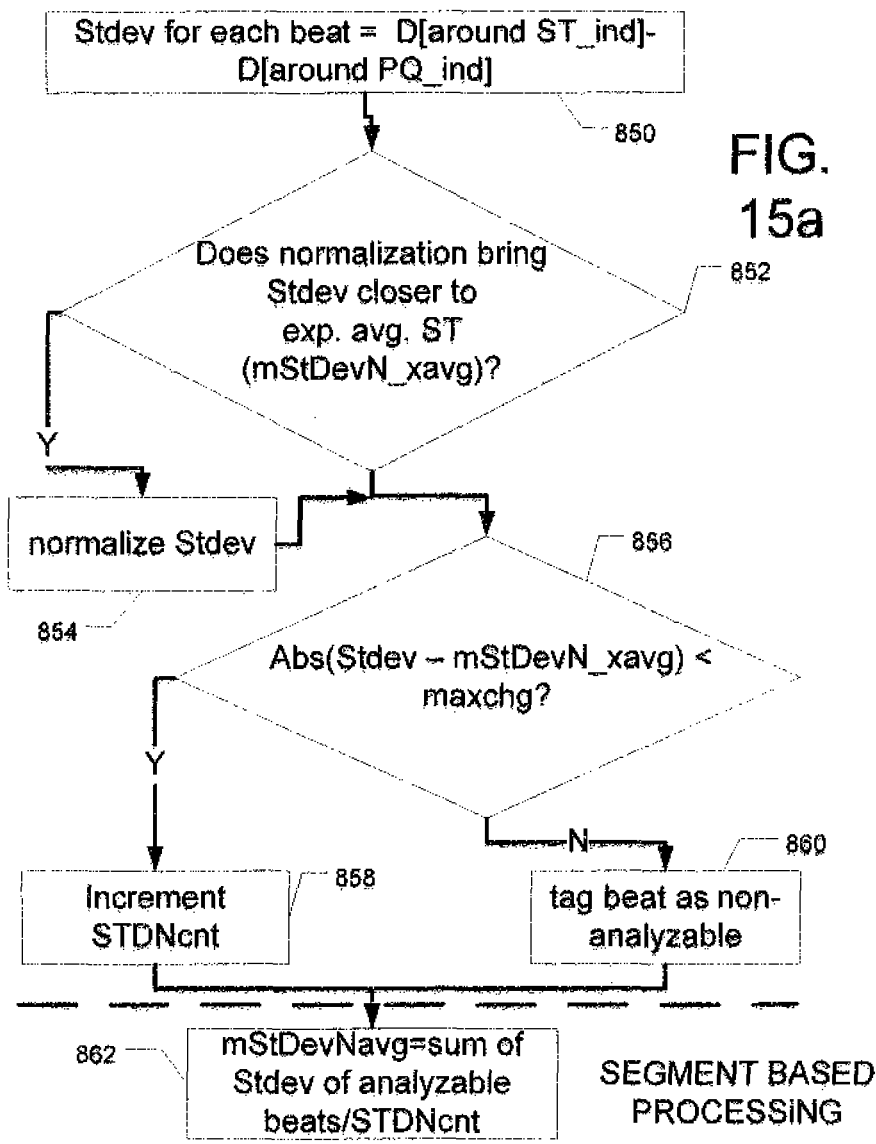
FIGS. 15*a*-15*b* are a flowchart that shows steps for determining a measure of segment based ST deviation and a long term exponential average filtered version of ST deviation.
Figure 15B:
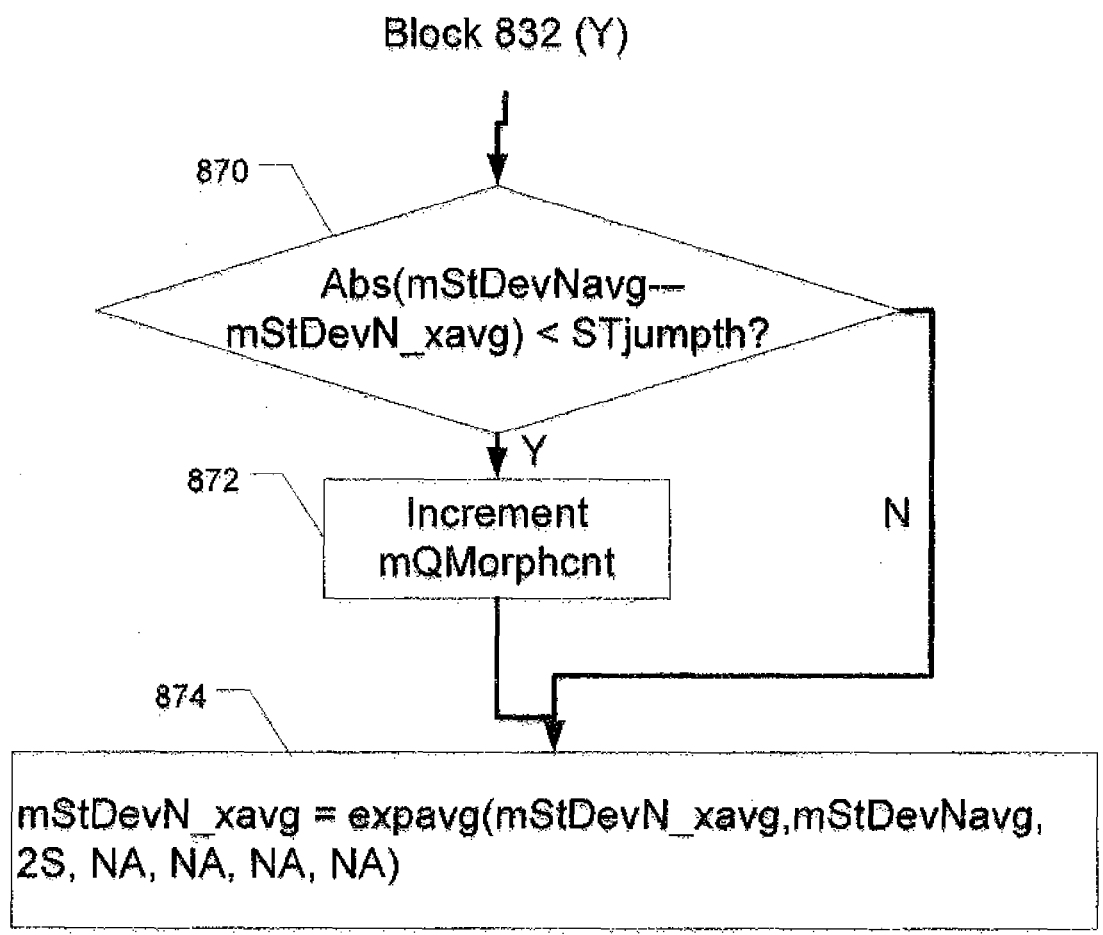

FIGS. 15a, and 15b are a flow chart of the preferred method for computing effective ST segment deviation (mStDevN_xavg), which is an averaged, filtered version of a number of beat based ST deviation measurements. FIG. 15a shows steps that are performed for each (provisionally) analyzable beat that has associated ST and PQ points, preferably determined according to the methods described in FIGS. 14a-14d and FIG. 17, respectively. In block 850, ST deviation (Stdev) is determined by the difference between the signal values of the samples surrounding the ST and PQ points, respectively. In the preferred embodiment, the PQ signal value is equal to the average of the signal over four consecutive samples starting at the sample that is two samples earlier than the PQ point. In the preferred embodiment, the ST signal value is equal to the average of the signal over four consecutive samples starting at the sample that is one sample earlier than the ST point.

Block 852 determines whether a normalized Stdev is closer to the existing long term averaged ST deviation (mStDevN_xavg). Normalization may be important due to amplitude changes in the signal that can result from a shift in patient postures or other causes, More than one type of normalization may be tried. The following are a preferred list of normalization possibilities, where QR is QRS amplitude, the maximum peak to peak amplitude of the QRS, and QR_sh and QR_long are short and long term exponential averages of QR, respectively: (1) normalize by multiplying Stdev by (QR_long/QR_short); (2) normalize by dividing ST_dev by QR_short (or multiplying by a decreasing function of QR like 1−QR_sh); (3) normalize by dividing ST_dev by a non-linear function of QR that saturates at high and low values of QR (or multiplying by a function that is an inverse of the non-linear function).

In an alternative embodiment, block 852 determines whether a normalized Stdev is closer to the existing normal ST deviation at the given RR interval based on past history histograms.

If normalization brings Stdev closer to then existing long term averaged ST deviation (mStDevN_xavg), then Stdev is normalized in block 854. Control passes to block 856, which checks whether the difference between Stdev and mStDevN$_{13}$ xavg exceeds a threshold. If so, the beat is tagged as non-analyzable in block 860 and does not figure into the segments average ST deviation. Otherwise, an analyzable ST deviation beat counter is incremented in block 858. The segment average ST deviation (mStDevNavg) is calculated in block 862.

Processing continues at block 870, shown in FIG. 15b if the test in block 832 (FIG. 14d) is satisfied. Block 870 checks whether the difference between mStDevNavg and the current long term, filtered ST time series (mStDevN_xavg) exceeds a threshold. If so, nQMorphent is incremented in block 872. Otherwise, control passes to block 874, which updates inStDevN_xavg based on mStDevNavg. The filtered change in mStDevNavg may also be computed based on the difference between the values of inStDeviNavg before (old_mStDevN_xavg) and after (mStDevN_xavg) the above mentioned update of mStDevN_xavg.

Figure 16:
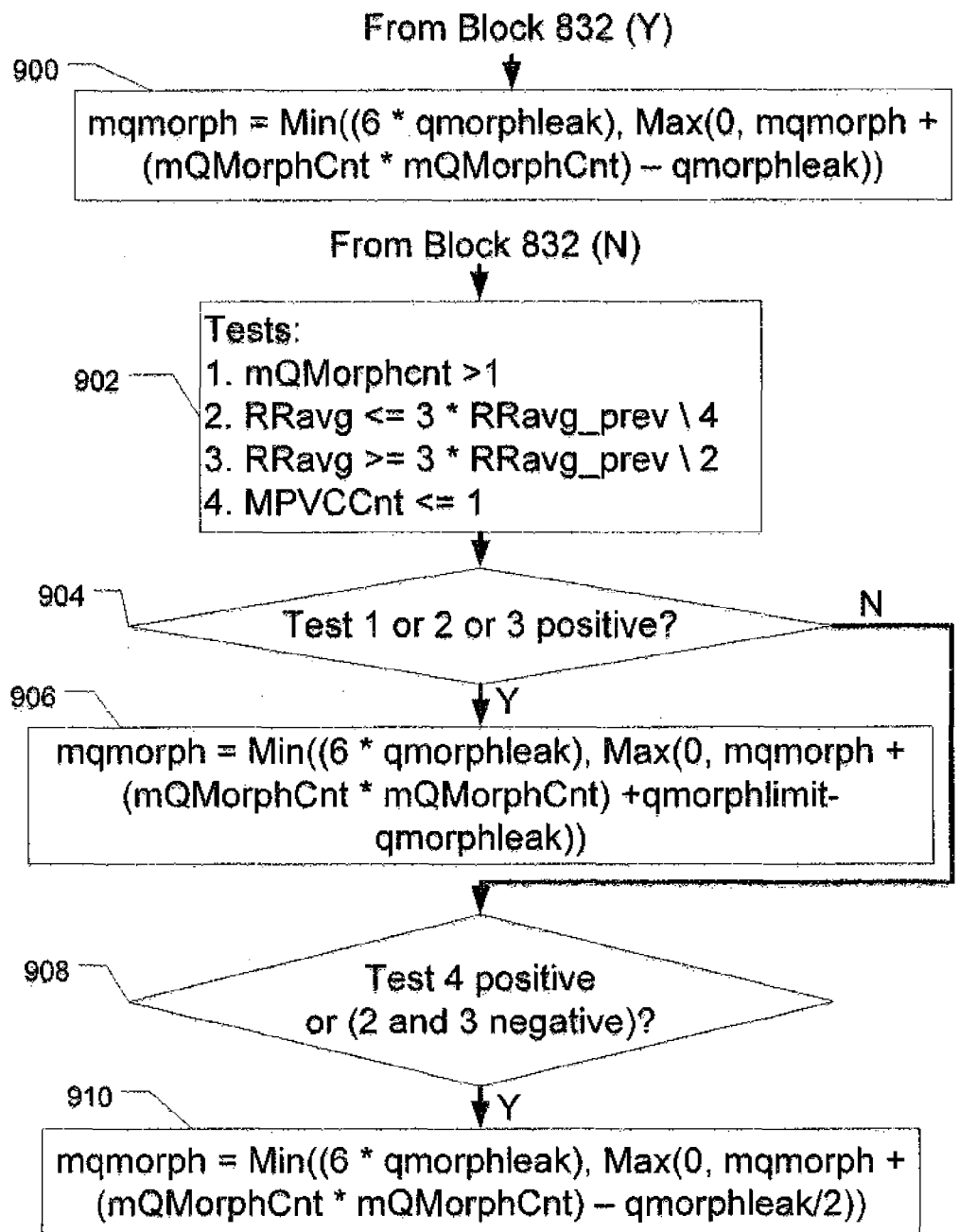
FIG. 16 is a flowchart of a routine that tracks the relative frequency of abnormal beats. Abnormal beats are determined according to QRS morphology, location of PQ and ST points, and the difference between ST deviation and long term average ST deviation. These beat based checks are performed in FIGS. 14*a*-14*d*, 15*a*-15*b* and 17.

FIG. 16 is a flow chart of a routine that tracks the relative frequency of variant beats. Variant beats are broadly defined as beats that deviate from an established pattern of normal sinus rhythm beats. Variant beats include beats that resulted in an increment of mQMoprhent during the QRS processing described with respect to FIG. 14a. As was described in connection with block 872 (FIG. 15b), mQMorphent is also updated if the average ST deviation of the segment, mStDevNavg, varies substantially from the filtered exponential average (mStDevN_xavg). Thus, sinus rhythm beats that result from an axis shift are considered variant. The relative frequency of variant beats is stored in a variable mqmorph. If mqmorph is above a threshold for a certain period of time, the system is preferably configured to respond in a user-programmable manner such as generating an alarm.

The mqmorph variable is updated after each segment is processed. The manner in which mqmoprh is updated depends on the outcome of the test applied in blocks 830 and 832 (FIG. 14d). If the outcome of this test suggests that the current segment is relatively "normal", mqmorph is computed in block 900. In particular, in block 900, mqmorph is increased by mQMorphCnt2−qmorphleak, subject to the constraints that mqmorph can not be negative or greater than 6*qmorphleak, where qmrophleak is a parameter. According to the above equation that updates mqmroph, qmorphleak acts like a "drain" that tends to "empty" mqmorph. Thus, mqmorph tends to remain at a low value unless there are a number of segments within a relatively short period of time with relatively high mQMorphCnts.

If the segment is considered relatively "abnormal" according to the test applied in blocks 830 and 832, control passes to blocks 902 and 904, which together implement another series of tests. If mQMorphent is greater than 1 or the segment's average RR interval is very different from the previous segment's RR interval, then mqmorph is increased in block 906 by mQMorphCnt2+qmorphlimit−qmorphleak, subject to the same constraints on the maximum and minimum mqmorph values described with respect to block 900.

Returning to block 904, if none of tests 1, 2 or 3 is positive, then control passes to block 908, which determines whether the RR interval is within ¾ and 1.5 time the previous RR interval, or the number of PVC's is low (less than 2). If so, block 910 increases mqmorph in the same manner as block 900 except that qmorphleak is divided by 2.

FIG. 17 is a flowchart that shows the preferred method for computing ST points. An analogous method may also be implemented to locate PQ points. In block 1002, the ST search window is set between maxQRS_ind+2 samples and maxQRS_ind+12 samples. In block 1004, the slope of the slope ("second finite difference") of the signal is computed by applying the same weighted sample averaging to the slope that was used to compute the slope itself (see discussion block 810 of FIG. 14b.). The search stops at the first sample at which the second finite difference is less than a specified multiple (ST_coef) of QR_xavg, an exponential average of QR (the peak to peak QRS amplitude, as previously described). In the preferred embodiment, ST_coef is −1, If such a qualifying sample is found (at sample k), block 1006 transfers control to block 1008, which sets the ST point (ST_ind) based on the value of k, subject to constraints on the location of the ST point. In particular, the ST point must be at least 2 samples after the Spt (defined in block 803 of FIG. 14a), and within a 3 sample window centered on Rpeak_ind+ST_int, where ST_int is an adaptive parameter that governs the location of the ST point.

Specifically, if k is within this three sample window, then the ST point (ST_ind) is chosen as the sample k. Otherwise, if k is before this window (i.e. closer to Spt than the beginning of this window), then ST_ind is set at the earliest sample in this window, Rpeak_ind+STint−1, subject to the previously mentioned constraint regarding the location of ST_ind relative to the Spt. If k is after the window, then then ST_ind is set at the latest sample in this window, Rpeak_ind+STint+1).

Block 1008 then transfers control to block 1012, which updates the adaptive parameter ST_int according to the number of samples between ST_ind and Rpeak. ST_int is preferably updated according to an exponential average filter.

Returning to block 1006, if no second finite difference within the ST point search window was less than the threshold, then control transfers to block 1010, which increments mQMorphent.

As is well known, integer based arithmetic, which is the preferred system for carrying out the operations described with reference to FIGS. 14-17, can produce undesirable results if the pertinent operands do not have sufficient granularity. for example, if 10 is divided by 6, the result is 1, compared to the desired result of 5/3. To reduce these types of problems, the data may be appropriate scaled. Continuing with the above example, if 10 is scaled up to 100 and then divided by 6, the result is 16, which (when divided by 10), is closer to the desired number 5/3. Appropriate scaling is performed to compare quantities that have been maintained at different scales. Continuing with the above example, if a threshold (to be applied to the value 10/6) is 2, it is scaled to 20, which may then be compared with the scaled value of 16.

For ease of understanding, the scaling factors (which are device and data dependent) have been omitted from the description of FIGS. 14-17. The preferred scaling factors for various quantities are as follows. With regard to FIGS. 15*a* and 15*b*, mStDevNavg and MStDevN_xavg are both scaled by a factor of 16. With regard to FIG. 17, ST_int and ST_ind−Rpeak_ind are scaled by a factor of 16 for purposes of computing the exponential average in block 1012. All. QR related quantities (used for ST deviation normalization and in block 1004 of FIG. 17) are scaled by a factor of 128.

The invention claimed is:

1. A cardiac monitor for estimating a value of a heart signal parameter, the monitor comprising:
   (a) a sensor for sensing an analog signal from a human heart;
   (b) a device coupled to the sensor, the device having analog-to-digital circuit system contained therein for digitizing the analog signal to produce a digitized waveform; and
   (c) a processor electrically coupled to the analog-to-digital circuit system, the processor configured to:
      (i) analyze the waveform to detect a plurality of beats;
      (ii) determine which of the plurality of beats meet analyzable beat criteria;
      (iii) determine a relative frequency of beats that meet the analyzable beat criteria;
      (iv) based on the relative frequency, determine whether to update a time series that tracks the value of a heart signal parameter;
      (v) operative when the time series is to be updated, updating the time series based on the output of a recursive filter, the filter having a first input that is based on a current value of the time series, the filter having a second input that is based on a current value of the heart signal parameter associated with a beat that meets the analyzable beat criteria.

2. The monitor of claim 1 wherein the plurality of beats are within a segment of waveform data having a fixed duration.

3. The monitor of claim 1 wherein the analyzable beat criteria include criteria pertaining to slopes within a QRS complex.

4. The monitor of claim 1 wherein the analyzable beat criteria include criteria pertaining to ST segment deviation.

5. The monitor of claim 1 wherein the determination whether to update the time series is further based on the average heart rate of the plurality of beats.

6. The monitor of claim 1 wherein the determination whether to update the time series is further based on a comparison between the average heart rate of the plurality of beats and the average heart rate of a prior plurality of beats.

7. The monitor of claim 1 wherein the processor is further determination whether to update the time series is further based on the relative number of premature ventricular contractions within the plurality of beats.

8. The monitor of claim 1 wherein the relative frequency is a function of the number of analyzable beats within a predetermined period.

9. The monitor of claim 1 wherein the processor is configured to determine an average value of the heart signal parameter for the plurality of beats, and wherein the second input to the filter is the average value of the heart signal parameter for the plurality of beats.

10. The monitor of claim 1 wherein the heart signal parameter is ST segment deviation.

11. A cardiac monitor for estimating a value of a heart signal parameter, the monitor comprising:
   (a) a sensor for sensing an analog signal from a human heart;
   (b) a device coupled to the sensor, the device having an analog-to-digital circuit system contained therein for digitizing the analog signal to produce a digitized waveform; and
   (c) a processor electrically coupled to the analog-to-digital circuit system, said processor configured to:
      (i) analyze the waveform to detect a plurality of beats;
      (ii) compute a time series that tracks the value of a heart signal parameter;
      (iii) measure the value of the heart signal parameter for a current beat that is one of the plurality of beats;
      (iv) compare the value of the heart signal parameter for the current beat with a current value Of the time series, and
      (v) if the value of the heart signal parameter for the current beat is sufficiently close to the current value of the time series, update the time series based on the output of a recursive filter, the filter having a first input that is based on a time series value, the filter having a second input that is based on the value of the heart signal parameter for the current beat.

\* \* \* \* \*